US010036055B2

(12) United States Patent
Church et al.

(10) Patent No.: US 10,036,055 B2
(45) Date of Patent: Jul. 31, 2018

(54) METHODS FOR MAKING NUCLEOTIDE PROBES FOR SEQUENCING AND SYNTHESIS

(71) Applicant: President and Fellows of Harvard College, Cambridge, MA (US)

(72) Inventors: George M. Church, Brookline, MA (US); Kun Zhang, Brighton, MA (US); Joseph Chou, Jamaica Plain, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 633 days.

(21) Appl. No.: 14/284,764

(22) Filed: May 22, 2014

(65) Prior Publication Data

US 2014/0349288 A1 Nov. 27, 2014

Related U.S. Application Data

(63) Continuation of application No. 12/187,460, filed on Aug. 7, 2008, now Pat. No. 8,771,950, which is a continuation of application No. PCT/US2007/003334, filed on Feb. 7, 2007.

(60) Provisional application No. 60/846,256, filed on Sep. 21, 2006, provisional application No. 60/765,978, filed on Feb. 7, 2006.

(51) Int. Cl.
*C12Q 1/68* (2018.01)
*C12Q 1/6813* (2018.01)
*C12Q 1/6837* (2018.01)

(52) U.S. Cl.
CPC ......... *C12Q 1/6813* (2013.01); *C12Q 1/6837* (2013.01); *C12Q 2535/113* (2013.01); *C12Q 2537/143* (2013.01); *C12Q 2565/543* (2013.01)

(58) Field of Classification Search
None
See application file for complete search history.

(56) References Cited

U.S. PATENT DOCUMENTS

| 4,683,195 | A | 7/1987 | Mullis et al. |
| 4,683,202 | A | 7/1987 | Mullis |
| 4,800,159 | A | 1/1989 | Mullis et al. |
| 4,883,750 | A | 11/1989 | Whiteley et al. |
| 4,965,188 | A | 10/1990 | Mullis et al. |
| 5,210,015 | A | 5/1993 | Gelfand et al. |
| 5,399,491 | A | 3/1995 | Kacian et al. |
| 5,866,337 | A | 2/1999 | Schon |

(Continued)

FOREIGN PATENT DOCUMENTS

| JP | 4262799 B2 | 5/2009 |
| WO | 2000058516 A2 | 10/2000 |

(Continued)

OTHER PUBLICATIONS

Feb. 19, 2010—(U.S.) Non-Final Office Action—U.S. Appl. No. 12/187,460.

(Continued)

*Primary Examiner* — Samuel C Woolwine
(74) *Attorney, Agent, or Firm* — Banner & Witcoff, Ltd.

(57) ABSTRACT

Compositions and methods for making a plurality of probes for analyzing a plurality of nucleic acid samples are provided. Compositions and methods for analyzing a plurality of nucleic acid samples to obtain sequence information in each nucleic acid sample are also provided.

24 Claims, 9 Drawing Sheets

(56) References Cited

U.S. PATENT DOCUMENTS

| | | | |
|---|---|---|---|
| 5,871,921 | A | 2/1999 | Landegren et al. |
| 5,942,391 | A * | 8/1999 | Zhang .................. C12Q 1/6816 |
| | | | 435/6.1 |
| 6,174,670 | B1 | 1/2001 | Wittwer et al. |
| 6,183,960 | B1 | 2/2001 | Lizardi |
| 6,183,967 | B1 | 2/2001 | Jayasena et al. |
| 6,235,472 | B1 | 5/2001 | Landegren et al. |
| 6,287,778 | B1 | 9/2001 | Huang et al. |
| 6,287,825 | B1 | 9/2001 | Weissman et al. |
| 6,344,239 | B1 | 2/2002 | Asai et al. |
| 6,432,360 | B1 | 8/2002 | Church |
| 6,485,944 | B1 | 11/2002 | Church et al. |
| 6,506,594 | B1 | 1/2003 | Barany et al. |
| 6,511,803 | B1 | 1/2003 | Church et al. |
| 6,709,816 | B1 | 3/2004 | Huang et al. |
| 6,858,412 | B2 | 2/2005 | Willis et al. |
| 2002/0182598 | A1 * | 12/2002 | Zhang .................... C12Q 1/682 |
| | | | 435/6.1 |
| 2003/0003490 | A1 | 1/2003 | Fan et al. |
| 2003/0104459 | A1 | 6/2003 | Faham et al. |
| 2003/0228611 | A1 | 12/2003 | Chruch et al. |
| 2004/0086892 | A1 * | 5/2004 | Crothers ................ C12Q 1/682 |
| | | | 435/6.12 |
| 2004/0101835 | A1 | 5/2004 | Willis et al. |
| 2004/0197800 | A1 | 10/2004 | Borns |
| 2004/0259226 | A1 | 12/2004 | Robey et al. |
| 2005/0037393 | A1 | 2/2005 | Gunderson et al. |
| 2005/0164207 | A1 | 7/2005 | Shapero |
| 2005/0176035 | A1 | 8/2005 | Crothers |
| 2006/0019304 | A1 * | 1/2006 | Hardenbol ........... C12Q 1/6837 |
| | | | 435/6.11 |
| 2007/0292861 | A1 * | 12/2007 | Thompson ........... C12Q 1/6816 |
| | | | 435/6.12 |

FOREIGN PATENT DOCUMENTS

| | | |
|---|---|---|
| WO | 2002/057491 | 7/2002 |
| WO | 2005/082098 A2 | 9/2005 |

OTHER PUBLICATIONS

Johan Banér et al., "Parallel gene analysis with allele-specific padlock probes and tag microarrays," Nucleic Acids Research, 2003, vol. 31, No. 17, e103, pp. 1-7.

Sep. 1 2010—(U.S.) Final Office Action—U.S. Appl. No. 12/187,460.

K. Zhang et al., "Sequencing genomes from single cells by polymerase cloning," Nature Biotechnology, vol. 24, No. 6, Jun. 2006, http://www.nature.com/naturebiotechnology.

P. Hardenbol et al., "Highly multiplexed molecular inversion probe genotyping: Over 10,000 targeted SNPs genotyped in a signle tube assay," Genome Res. 2005, 15: 269-275.

C.A. Hutchison III et al., "Cell-free cloning using ø29 DNA polymerase," 17332-17336, PNAS, Nov. 29, 2005, vol. 102, No. 48.

Y. Wang et al.,"Allele quantification using molecular inversion probes (MIP)," Nucleic Acids Research, 2005, vol. 33, No. 21, e183, pp. 1-14.

A.D. Bates et al., "DNA gyrase can supercoil DNA circles as small as 174 base pairs," The EMBO Journal, vol. 8, No. 6, pp. 1861-1866, 1989.

H. Yan et al., "Allelic Variation in Human Gene Expression," Science, vol. 297, Aug. 16, 2002, p. 1143, www.sciencemag.org.

J. Tian et al., "Accurate multiplex gene synthesis from programmable DNA microchips," Nature, vol. 432, Dec. 23-30, 2004, pp. 1050-1054, www.nature.com/nature.

Ann-Christine Syv?nen, "Toward genome-wide SNP genotyping," Nature Genetics Supplement, vol. 37, Jun. 2005, pp. S5-S10.

J.M. Shumaker et al., "Mutation Detection by Solid Phase Primer Extension," Human Mutation 7:346-354 (1996).

P. Hardenbol et al., "Multiplexed genotyping with sequencing-tagged molecular inversion probes," Nature Biotechnology, vol. 21, No. 6, Jun. 2003, pp. 673-678.

M. Nilsson et al., "Padlock Probes: Circularizing Oligonucleotides for Localized DNA Detection," Science, vol. 25, Sep. 30, 1994, pp. 2085-2088.

J. Banér et al., "Signal amplification of padlock probes by rolling circle replication," Nucleic Acids Research, 1998, vol. 26, No. 22, pp. 5073-5078.

P.M. Lizardi et al., "Mutation detection and single-molecule counting using isothermal rolling-circle amplification," Nature Genetics, vol. 19, Jul. 19, 1998, pp. 225-232.

N.P. Gerry et al., "Universal DNA Microarray Method for Multiplex Detection of Low Abundance Point Mutations," J. Mol. Biol. (1999), 292, 251-262, http://www.idealibrary.com.

J.B. Fan et al., "Parallel Genotyping of Human SNPs Using Generic High-density Oligonucleotide Tag Arrays," Genome Research, 2000, 10:853-860.

G. Leone et al., "Molecular beacon probes combined with amplification by NASBA enable homogeneous, real-time detection of RNA," Nucleic Acids Research, 1998, vol. 26, No. 9, pp. 2150-2155.

F. Dahl et al., "Circle-to-circle amplification for precise and sensitive DNA analysis," 4548-4553, PNAS, Mar. 30, 2004, vol. 101, No. 13.

Sep. 26, 2008—International Search Report and Written Opinion received in corresponding Application No. PC/Us2007/03334.

* cited by examiner

M: Linear oligo (83bp)
H: Helper oligo (35bp)
A1: AmpLigase, 95C 5min, 50C 15min
A2: AmpLigase, 5x (94C 30sec, 50C 3min)
C1: CircLigase
C2: CircLigase in 1M Betaine M: 10bp ladders
1: AmpLigase, 10nM oligo, 10nM helper
2: AmpLigase, 10nM oligo, 30nM helper
3: AmpLigase, 10nM oligo, 100nM helper
4: T4 DNA Ligase, 10nM oligo, 10nM helper
5: T4 DNA Ligase, 10nM oligo, 30nM helper
6: T4 DNA Ligase, 10nM oligo, 100nM helper
R: Linear oligo (70bp)

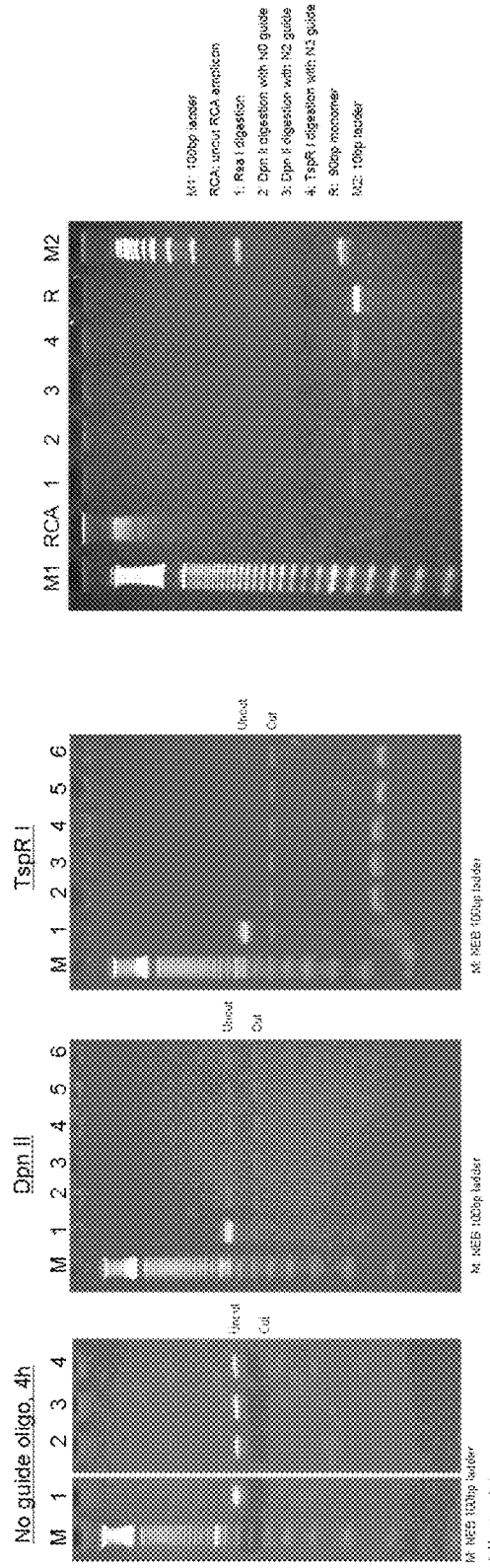

SEQUENCE LISTING

```
<160> NUMBER OF SEQ ID NOS: 4

<210> SEQ ID NO 1
<211> LENGTH: 89
<212> TYPE: DNA
<213> ORGANISM: Artificial
<220> FEATURE:
<223> OTHER INFORMATION: Template oligonucleotide
<220> FEATURE:
<221> NAME/KEY: misc_feature
<222> LOCATION: (23)..(30)
<223> OTHER INFORMATION: wherein n is g, a, t or c
<220> FEATURE:
<221> NAME/KEY: misc_feature
<222> LOCATION: (61)..(68)
<223> OTHER INFORMATION: wherein n is g, a, t or c

<400> SEQUENCE: 1
ttgggacata tcggtcagtg atnnnnnnnn cgttcctatt cggtcgagca aatgttatcg     60
nnnnnnnnga tcaggataca cactacccg                                      89

<210> SEQ ID NO 2
<211> LENGTH: 25
<212> TYPE: DNA
<213> ORGANISM: Artificial
<220> FEATURE:
<223> OTHER INFORMATION: Guide oligonucleotide
<220> FEATURE:
<221> NAME/KEY: misc_feature
<222> LOCATION: (23)..(25)
<223> OTHER INFORMATION: wherein n is g, a, t or c

<400> SEQUENCE: 2
aaccctgtat agccagtcac tannn                                          25

<210> SEQ ID NO 3
<211> LENGTH: 13
<212> TYPE: DNA
<213> ORGANISM: Artificial
<220> FEATURE:
<223> OTHER INFORMATION: Guide oligonucleotide

<400> SEQUENCE: 3
ctagtcctat gtg                                                       13

<210> SEQ ID NO 4
<211> LENGTH: 15
<212> TYPE: DNA
<213> ORGANISM: Artificial
<220> FEATURE:
<223> OTHER INFORMATION: Guide oligonucleotide
<220> FEATURE:
<221> NAME/KEY: misc_feature
<222> LOCATION: (1)..(2)
<223> OTHER INFORMATION: wherein n is g, a, t or c
```

```
<400> SEQUENCE: 4
nnctagtcct atgtg                                                              15
```

METHODS FOR MAKING NUCLEOTIDE PROBES FOR SEQUENCING AND SYNTHESIS

RELATED U.S. APPLICATIONS

This application is a continuation of U.S. application Ser. No. 12/187,460 (pending), filed Aug. 7, 2008, which is a continuation of PCT application no. PCT/US2007/003334, designating the United States and filed Feb. 7, 2007; which claims the benefit U.S. Provisional Patent Application No. 60/846,256, filed on Sep. 21, 2006; and U.S. Provisional Patent Application No. 60/765,978, filed on Feb. 7, 2006; each of which is hereby incorporated herein by reference in its entirety for all purposes.

STATEMENT OF GOVERNMENT INTERESTS

This application was funded in part by National Institutes of Health Grant No. HG003170 and Department of Energy Grant No. DE-FG02-02ER63445. The government has certain rights to the invention.

BACKGROUND OF THE INVENTION

Field of the Invention

Embodiments of the present invention relate in general to the use of molecular inversion probe technology in capture sequence methods and amplification methods.

Description of Related Art

Molecular Inversion Probe ("MIP") technology is a high-throughput genotyping technology capable of interrogating single nucleotide polymorphisms on a large scale. Methods of using molecular inversion probe technology in highly multiplexed genotyping of SNPs are known. See Hardenbol et al. *Genome Res.* (2005) 15:269 and Hardenbol et al. (2003) *Nat. Biotechnol.* 21:673. The use of molecular inversion probe technology in allele quantification is also known. See Wang et al. (2005) *Nucl. Acids Res.* 33(21).

Generally, MIP technology is directed to the use of a single oligonucleotide probe with recognition sequences at each terminus. The probe also includes a specific tag sequence that is ultimately read on a microarray, and two PCR primers that face away from each other and therefore cannot facilitate amplification. The probe is hybridized with a genomic target sequence such that it forms a circular structure, with the ends of the probe abutting. This leaves a single base gap at the location of a SNP. This gapped-duplex is then tested in four separate reactions, each with a single dNTP species present, in which successful polymerization and ligation provides allelic differentiation. The probes are subsequently released from the genomic DNA and those that have been covalently circularized in the correct allele/nucleotide reaction combination are amplified using a "universal" PCR primer pair. Each amplified probe contains a unique tag array referred to here as "barcoding." Tags are selected to have a similar $T_m$ and base composition and to be maximally orthogonal in sequence complementarity. Amplicons are fluorescently labeled and the tag sequences released from the genome homology regions using a restriction endonuclease treatment. The tags are then detected using a complementary tag array.

BRIEF SUMMARY OF THE INVENTION

Embodiments of the present invention are directed to methods of making large numbers of amplifiable oligonucleotide probes using microarray technology. The probes are useful in methods of capturing a single base, multiples bases and/or larger regions of DNA for amplification (e.g., by emulsion PCR) by methods including polymerized colony sequencing. In certain aspects of the invention, probes include padlock probes, rolling circle probes and/or molecular inversion probes. According to a certain aspect of the invention, a barcode sequence is used to uniquely tag each oligonucleotide sample from a patient so that a large number of loci in a large number of DNA samples can be analyzed in one or more polymerase colony sequencing runs. According to an alternate embodiment of the present invention, a set of oligonucleotide probes, once synthesized, can repeatedly be used in unlimited applications through PCR amplification with universal primers. Alternatively, amplification can also take place with locus-specific primers that flank the region of interest, especially when capturing genomic sequences from patient samples. Such a region of interest includes a specific target sequence that may be associated with a disease-associated polymorphism. Embodiments of the present invention include capture of multiple markers using a set of primer pairs. Also, when non-specific DNA sequences are to be captured, some randomization is desirable in the primer pool for example to amplify the same region from various homologs/orthologs of a given gene in a subject patient.

In one embodiment, a method of making a plurality of probes for analyzing a plurality of nucleic acid samples is provided. The method includes the steps of providing linear, single stranded DNA encoding a plurality of probes, wherein a probe includes two regions of homology to target genomic DNA at the ends of the probe and two PCR primer regions common to all probes, converting the linear, single stranded DNA to circular DNA, amplifying the circular DNA, and releasing (e.g., by digestion with a restriction endonuclease or a combination of uracil DNA glycosylase and DNA glycosylase-lyase Endonuclease VIII) the plurality of probes from the amplified DNA. In certain aspects, the step of converting is performed using a DNA ligase that catalyzes intra-molecular ligation of single stranded DNA or using a double stranded DNA ligase in the presence of an oligonucleotide sequence. In certain aspects, one or more portions of the probe encode a bar code specific for a nucleic acid sample sequence. In other aspects, the step of amplifying the circular DNA is performed by rolling circle amplification. In other aspects, prior to the step of converting, the linear, single stranded DNA is amplified using Bst polymerase or Phi29 polymerase and/or PCR. In other aspects, prior to the step of converting, the linear, single stranded DNA is purified by size selection. In yet other aspects, the plurality of nucleic acid samples are genomic DNA regions (e.g., exons, single nucleotide polymorphisms, mutable regions and/or highly conserved regions), mRNA and/or cDNA. In other aspects, the linear, single stranded DNA is synthesized on a DNA chip. In still other aspects, the PCR primer regions are removed from the probes by digestion with a restriction endonuclease or a combination of uracil DNA glycosylase and DNA glycosylase-lyase Endonuclease VIII.

In another embodiment, a method of making a plurality of probes is provided, including the steps of providing linear, single stranded DNA encoding a plurality of probes, wherein a probe includes two regions of homology to target genomic DNA at the ends of the probe and two PCR primer regions common to all probes, converting the linear, single stranded DNA to circular DNA, amplifying the circular DNA to form amplified double stranded, circular DNA, converting the amplified double stranded, circular DNA to single stranded, circular DNA, and releasing the plurality of probes from the single stranded, circular DNA. In certain aspects, the step of releasing is performed by digestion with a restriction endonuclease. In other aspects, the step of converting the linear, single stranded DNA to circular DNA is performed using a DNA ligase that catalyzes intra-molecular ligation of single stranded DNA and/or using a double stranded DNA ligase in the presence of an oligonucleotide sequence. In other aspects, one or more portions of the probe further encode a bar code specific for a nucleic acid sample sequence. In other aspects, the step of amplifying the circular DNA is performed by rolling circle amplification. In yet other aspects, prior to the step of converting, the linear, single stranded DNA is amplified using Bst polymerase or Phi29 polymerase and/or by PCR. In other aspects, prior to the step of converting, the linear, single stranded DNA is amplified by PCR. In other aspects, prior to the step of converting, the linear, single stranded DNA is purified by size selection. In still other aspects, the plurality of nucleic acid samples are genomic DNA regions (e.g., exons, single nucleotide polymorphisms, mutable regions and/or highly conserved regions), mRNA and/or cDNA. In certain aspects, the linear, single stranded DNA is synthesized on a DNA chip. In yet other aspects, the PCR primer regions are removed from the probes by digestion with a restriction endonuclease or a combination of uracil DNA glycosylase and DNA glycosylase-lyase Endonuclease VIII.

In another embodiment, a method of making a renewable pool of probes for analyzing a plurality of nucleic acid samples is provided. The method includes the steps of providing a plurality of linear, single stranded DNA probes, wherein a probe includes two regions of homology to target genomic DNA at its ends, two PCR primer regions common to all probes and a unique endonuclease recognition site, converting the linear, single stranded DNA to circular DNA, amplifying the circular DNA by rolling circle amplification to form linear concatemers, digesting the linear concatemers with an endonuclease in the presence of a guide oligonucleotide to form monomers, and ligating the monomers to form a plurality of circular molecules complementary to either the plus strand or the minus strand of the circular DNA. In certain aspects, the plurality of linear, single stranded DNA probes are synthesized on a programmable DNA chip. In other aspects, the renewable pool of probes is a renewable library.

In another embodiment, a method of selectively capturing a plurality of genomic sequences is provided. The method includes the steps of providing a probe having two regions of homology to target genomic DNA at the ends of the probe, two common priming regions, and a restriction endonuclease recognition site, hybridizing the probe to immobilized genomic DNA such that the probe is hybridized in a circular manner to complementary genomic DNA, ligating the probe to produce a closed circular molecule, separating the closed circular molecule from the genomic DNA, and amplifying the closed circular molecule. In certain aspects, the genomic sequence is selected from the group consisting of exons, single nucleotide polymorphisms, mutable regions and highly conserved regions.

In another embodiment, a method of analyzing a plurality of genomic DNA samples to obtain sequence information at one or more loci in each genomic DNA sample is provided. The method includes the steps of providing one or more probes having two regions of homology to target genomic DNA at the ends of the probe, two PCR primer regions common to all probes, and a bar code specific for a locus, hybridizing the probes to immobilized genomic DNA such that the probe is hybridized in a circular manner to complementary genomic DNA, ligating the probe to produce a closed circular molecule, separating the closed circular molecule from the genomic DNA, and amplifying the closed circular molecule. In certain aspects, the method further includes the step of digesting unligated products after the step of ligating and before the step of removing. In other aspects, the method further includes the step of cleaving the amplified closed circular molecule. In certain aspects, amplifying is performed by a method selected from the group consisting of PCR (e.g., ePCR), rolling circle amplification and hyper-branched rolling circle amplification. In other aspects, the PCR primer regions are ePCR primer regions. In other aspects, the PCR primer regions further comprise a bar code specific for a patient. In still further aspects, cleaving is performed by a restriction enzyme. In yet other aspects, the one or more probes further comprise a universal detection tag sequence. In still further aspects, the method also includes the step of polony amplification and/or polony sequencing.

In another embodiment, a method of analyzing a plurality of genomic DNA samples to obtain sequence information at one or more loci in each genomic DNA sample is provided. The method includes the steps of providing one or more probes having two regions of homology to target genomic DNA at the ends of the probe, two PCR primer regions common to all probes, a bar code specific for a locus and a bar code specific for a patient, contacting the probes with genomic DNA to hybridize the probe in a circular manner to complementary genomic DNA, covalently attaching the extension to the end of the probe in the presence of a ligase to produce a closed circular molecule, and amplifying the circular molecule. In certain aspects, amplifying is performed by PCR (e.g., by ePCR). In other aspects, the PCR primer regions are ePCR primer regions. In certain aspects, cleaving is performed using a restriction enzyme. In other aspects, the one or more probes further comprise a unique tag sequence. In still further aspects, the method also includes the step of polony amplification and/or polony sequencing.

In another embodiment, a method for enriching a probe pool for analyzing a plurality of genomic DNA regions in a genomic DNA sample, the method comprising the steps of providing a plurality of probes each having two regions of degenerate homology to target genomic DNA at the ends of each probe, two PCR primer regions common to each probe, and a bar code specific for a genomic DNA region, hybridizing the probes to genomic DNA such that the probe is hybridized in a circular manner to complementary genomic DNA, ligating the probe to produce a closed circular molecule, separating the closed circular molecule from the genomic DNA, and amplifying the closed circular molecule is provided. In certain aspects, the plurality of genomic DNA regions are regions selected from the group consisting of exons, single nucleotide polymorphisms, mutable regions and highly conserved regions. In other aspects, the step of digesting unligated products after the step of ligating and before the step of removing.

In another embodiment, a method of analyzing a plurality of mRNA samples to obtain allele-specific quantitation at one or more alleles in each mRNA sample is provided. The method includes the steps of providing one or more probes having two regions of homology to target mRNA at the ends of the probe, two PCR primer regions common to all probes, a bar code specific for an allele, and a bar code specific for a patient, contacting the probes with mRNA to hybridize the probe in a circular manner to complementary mRNA, ligating the probe to produce a closed circular molecule, separating the closed circular molecule from the mRNA, and amplifying the closed circular molecule.

In another embodiment, a method of analyzing a plurality of cDNA samples to obtain allele-specific quantitation at one or more alleles in each cDNA sample is provided. The method includes the steps of providing one or more probes having two regions of homology to target cDNA at the ends of the probe, two PCR primer regions common to all probes, a bar code specific for an allele, and a bar code specific for a patient, contacting the probes with cDNA to hybridize the probe in a circular manner to complementary cDNA, ligating the probe to produce a closed circular molecule, removing the closed circular molecule from the cDNA, and amplifying the closed circular molecule.

In another embodiment, a method of selectively capturing a plurality of genomic sequences is provided. The method includes the steps of providing a probe having two regions of homology to target genomic DNA at the ends of the probe, two common priming regions, and a restriction endonuclease recognition site, hybridizing the probe to immobilized genomic DNA such that the probe is hybridized in a circular manner to complementary genomic DNA, polymerizing the extension of the probe in the presence of dATP, dCTP, dGTP or dTTP and a polymerase, ligating the probe to produce a closed circular molecule, separating the closed circular molecule from the genomic DNA, and amplifying the closed circular molecule. In certain aspects, the genomic sequence is selected from the group consisting of exons, single nucleotide polymorphisms, mutable regions and highly conserved regions.

In another embodiment, a method of analyzing a plurality of genomic DNA samples to obtain sequence information at one or more loci in each genomic DNA sample, the method comprising the steps of providing one or more probes having two regions of homology to target genomic DNA at the ends of the probe, two PCR primer regions common to all probes, and a bar code specific for a locus, hybridizing the probes to immobilized genomic DNA such that the probe is hybridized in a circular manner to complementary genomic DNA with a one or more nucleotide gap between the ends of the circularized probe, polymerizing the extension of the probe in the presence of dATP, dCTP, dGTP or dTTP and a polymerase, ligating the probe to produce a closed circular molecule, separating the closed circular molecule from the genomic DNA, and amplifying the closed circular molecule is provided. In certain aspects, the method further includes the step of digesting unligated products after the step of ligating and before the step of removing. In other aspects, the method further includes the step of cleaving the amplified closed circular molecule. In certain aspects, amplifying is performed by a method selected from the group consisting of PCR (e.g., ePCR), rolling circle amplification and hyperbranched rolling circle amplification. In other aspects, the PCR primer regions are ePCR primer regions. In other aspects, the PCR primer regions further comprise a bar code specific for a patient. In other aspects, cleaving is performed by a restriction enzyme. In yet other aspects, the one or more probes further comprise a universal detection tag sequence. In still further aspects, the method also includes the step of polony amplification and/or polony sequencing.

In another embodiment, a method of analyzing a plurality of genomic DNA samples to obtain sequence information at one or more loci in each genomic DNA sample, the method comprising the steps of providing one or more probes having two regions of homology to target genomic DNA at the ends of the probe, two PCR primer regions common to all probes, a bar code specific for a locus and a bar code specific for a patient, contacting the probes with genomic DNA to hybridize the probe in a circular manner to complementary genomic DNA with a one or more nucleotide gap between the ends of the circularized probe, polymerizing the extension of the probe in the presence of dATP, dCTP, dGTP or dTTP and a polymerase, covalently attaching the extension to the end of the probe in the presence of a ligase to produce a closed circular molecule, and amplifying the circular molecule is provided. In certain aspects, amplifying is performed by PCR (e.g., by ePCR). In other aspects, the PCR primer regions are ePCR primer regions. In still other aspects, cleaving is performed using a restriction enzyme. In other aspects, the one or more probes further comprise a unique tag sequence. In still further aspects, the method also includes the step of polony amplification and/or polony sequencing.

In another embodiment, a method for enriching a probe pool for analyzing a plurality of genomic DNA regions in a genomic DNA sample, the method comprising the steps of providing a plurality of probes each having two regions of degenerate homology to target genomic DNA at the ends of each probe, two PCR primer regions common to each probe, and a bar code specific for a genomic DNA region, hybridizing the probes to genomic DNA such that the probe is hybridized in a circular manner to complementary genomic DNA with a one or more nucleotide gap between the ends of the circularized probe, polymerizing the extension of the probe in the presence of dATP, dCTP, dGTP or dTTP and a polymerase, ligating the probe to produce a closed circular molecule, separating the closed circular molecule from the genomic DNA, and amplifying the closed circular molecule is provided. In certain aspects, the plurality of genomic DNA regions are regions selected from the group consisting of exons, single nucleotide polymorphisms, mutable regions and highly conserved regions. In other aspects, the method further includes the step of digesting unligated products after the step of ligating and before the step of removing.

In another embodiment, a method of analyzing a plurality of mRNA samples to obtain allele-specific quantitation at one or more alleles in each mRNA sample, the method comprising the steps of providing one or more probes having two regions of homology to target mRNA at the ends of the probe, two PCR primer regions common to all probes, a bar code specific for an allele, and a bar code specific for a patient, contacting the probes with mRNA to hybridize the probe in a circular manner to complementary mRNA with a one or more nucleotide gap between the ends of the circularized probe, polymerizing the extension of the probe in the presence of dATP, dCTP, dGTP or dTTP and a polymerase, ligating the probe to produce a closed circular molecule, separating the closed circular molecule from the mRNA, and amplifying the closed circular molecule is provided.

In another embodiment, a method of analyzing a plurality of cDNA samples to obtain allele-specific quantitation at one or more alleles in each cDNA sample, the method comprising the steps of providing one or more probes having two regions of homology to target cDNA at the ends of the probe, two PCR primer regions common to all probes, a bar code specific for an allele, and a bar code specific for a patient, contacting the probes with cDNA to hybridize the probe in a circular manner to complementary cDNA with a one or more nucleotide gap between the ends of the circularized probe, polymerizing the extension of the probe in the presence of dATP, dCTP, dGTP or dTTP and a polymerase, ligating the probe to produce a closed circular molecule, removing the closed circular molecule from the cDNA, and amplifying the closed circular molecule is provided.

Advantages of the embodiments of the present invention include efficiencies of economy and increases in the number of loci and samples analyzed simultaneously. Applications of the present invention extend to large-scale SNP genotyping, mutation discovery, exon or other DNA sequence resequencing (e.g., of cancer genomic DNA), quantification of allelic specific gene expression and analysis of synthetic genomes. Embodiments of the present invention also relate to multiplex circular probe formation for sequencing and/or multiplex synthesis.

Further features and advantages of certain embodiments of the present invention will become more fully apparent in the following description of the embodiments and drawings thereof, and from the claims.

BRIEF DESCRIPTION OF THE DRAWINGS

FIGS. 8A-8C depict the characterization of restriction endonucleases for releasing padlock probes. (A) shows a schematic synthetic template (SEQ ID NO:1) and guide oligos (SEQ ID NOs:2-4. To mimic a complex pool of chip-synthesized oligonucleotide, a 90 base pair oligonucleotide containing two degenerate regions was synthesized by the conventional column-based method at IDT. Three guide oligos were designed for restriction endonuclease digestions. (B) shows digestion of the IDT-synthesized template indicating that Dpn II, TspR I and Taqα I do not have activity on single-stranded DNA without guide oligos (left panel). Dpn II and TspR I cut at specific sites in the presence of guide oligos in different reaction buffers (middle and right panel). (C) shows oligo-guided restriction enzyme digestion on RCA amplicons. The 90 base pair oligonucleotide was circularized, amplified with RCA, and digested in the presence of guide oligos. The Rsa I site was introduced during circularization, and will be used for another purpose (making a renewable pool).

DETAILED DESCRIPTION

Figure 1:
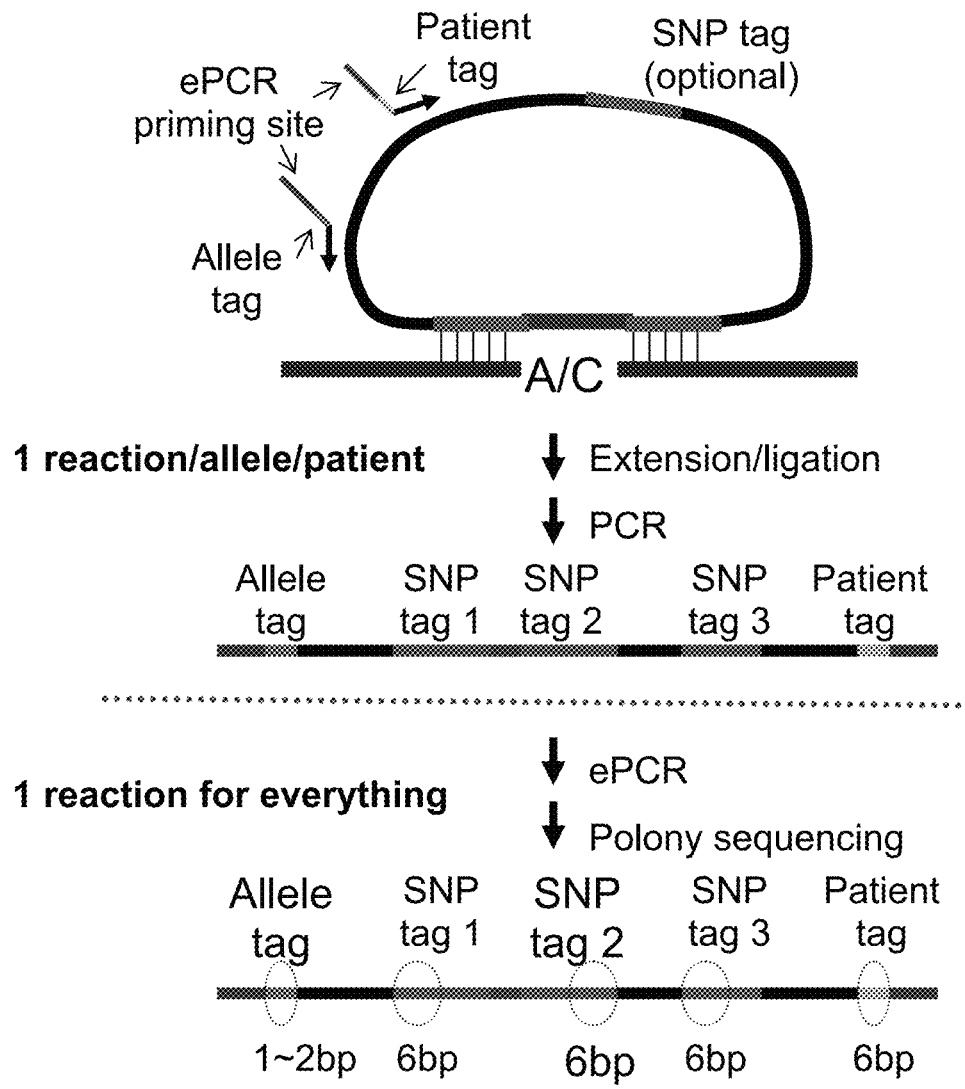
FIG. 1 schematically depicts an assay designed to ascertain many SNPs across many patients.

The principles of the present invention may be applied with particular advantage in methods of generating large numbers of amplifiable oligonucleotide probes using molecular inversion probe technology. Probe designs having a fixed gap length of one nucleotide and using barcoding sequences according to the present invention allow simple single nucleotide polymorphism ("SNP") assays to identify many SNPs for many patients in a single assay run. Probe designs having a gap length greater than one base and using barcoding sequences are also useful in SNP assays or other DNA assays in which it is desirable to capture longer target DNA sequences.

According to aspects of the present invention, molecular inversion probes are used based on the methods described in Hardenbol, *Nature Biotech.*, Vol. 21, No. 6., 6 Jun. 1993, Hardenbol et al., *Genome Research*, 2005; 15(2):269-75; Fakhrai et al. (2003) *Nature Biotech.* 21(6):673 and Wang et al. (2005) *Nucl. Acids Res.* 33:e183. For SNP detection, a single probe is used to detect both alleles of each SNP. The probe includes two regions of homology to target genomic DNA located at the termini or end of the probe, two PCR primer regions common to all probes, one bar code specific for each locus, and two common cleavage sites. According to the present invention, the probe may also contain a barcode identifying each patient or other subject. A universal detection tag sequence is used for array detection of amplified probe. Cleavage sites are used to release the circularized probe from genomic DNA and for post-amplification processing.

According to the present invention, a mixture of genomic DNA, a plurality of probes and thermostable ligase and polymerase is heat denatured and brought to annealing temperature. Two sequences targeting each terminus of the probe hybridize to complementary sites in the genomic DNA, creating a circular conformation with a single-nucleotide gap between the termini of the probe. According to an alternate embodiment, the gap may be greater than one nucleotide. The genomic DNA is then split into four separate samples. Unlabeled dATP, dCTP, dGTP or dTTP is added to each of four samples. In reactions where the added nucleotide is complementary to the single base gap, DNA polymerase adds the nucleotide and DNA ligase closes the gap to form a covalently closed circular molecule that encircles the genomic strand to which it is hybridized. Exonucleases are added to digest linear probes in reactions where the added nucleotide was not complementary to the gap and excess linear probe in reactions where circular molecules were formed. The reactions are then heated to inactivate the exonucleases. To release probes from genomic DNA, uracil-N-glycosylase is added to depurinate the uracil residues in the probes. The mixture is then heated to cleave the molecule at the abasic site and release it from genomic DNA. Alternatively, the molecule can be removed from the genomic DNA through methods other than cleavage, thereby leaving the molecule in its circular form. PCR reagents can then be added, including a primer pair common to all probes, or the hybridization primer sequences and their complements can be used in the amplification step. The reactions are then subjected to thermal cycling, with the result that only probes circularized in the allele-specific gap-fill reaction are amplified. Rolling circle amplification, when the probe remained circular, may also be used with certain probe embodiments of the invention.

According to certain aspects of the present invention, molecular inversion probes can be manufactured having gaps larger than one nucleotide and without extending the length of the molecular inversion probe. According to one aspect, the single stranded regions of the MIP during ligation reaction are free to extend far beyond the usual 0.34 nm/base and are free to rotate, unlike perfect CCC. Alternatively, very small DNA circles can be made according to the methods described in Bates et al. (1989) *EMBO J.* 8:1861.

According to the present invention, smaller MIP probes aimed at large targets are believed to perform better in the range of 300 to 900 base pairs, which is advantageous for exons and other conserved elements. Once the circular probes are ligated, and non-ligated material removed by exonuclease or other means, then the circular probes can be amplified by PCR as described in Hardenbol (supra) and/or by using isothermal strand-displacement amplification.

FIG. 1 describes in schematic one embodiment of an assay of the present invention designed to ascertain many SNPs across many patients. As can be seen, a molecular inversion probe is hybridized to a strand of genomic DNA, which may be attached to the surface of a microarray. The molecular inversion probe includes two ePCR priming sites. As used herein, the term ePCR would be understood by one of skill in the art to refer to "emulsion PCR."

One ePCR priming site is attached to an allele tag while the other ePCR priming site is attached to a patient tag. An SNP tag is shown as being optional. The two ends of the probe are hybridized to genomic DNA with a fixed gap length of one nucleotide. The gap length is filled by an appropriate nucleotide using standard extension reagents such as DNA polymerase and dATP, dCTP, dGTP or dTTP. The ends of the probe are then ligated using an appropriate DNA ligase. The probe is then amplified, such as by using PCR, to produce an amplicon for each allele per patient. Alternatively, as shown in FIG. 1, ePCR is used followed by polymerized colony sequencing, referred to as "polony sequencing." The method provides a very simple assay to assay millions of SNPs in hundreds of patients in one experimental run.

Figure 2:
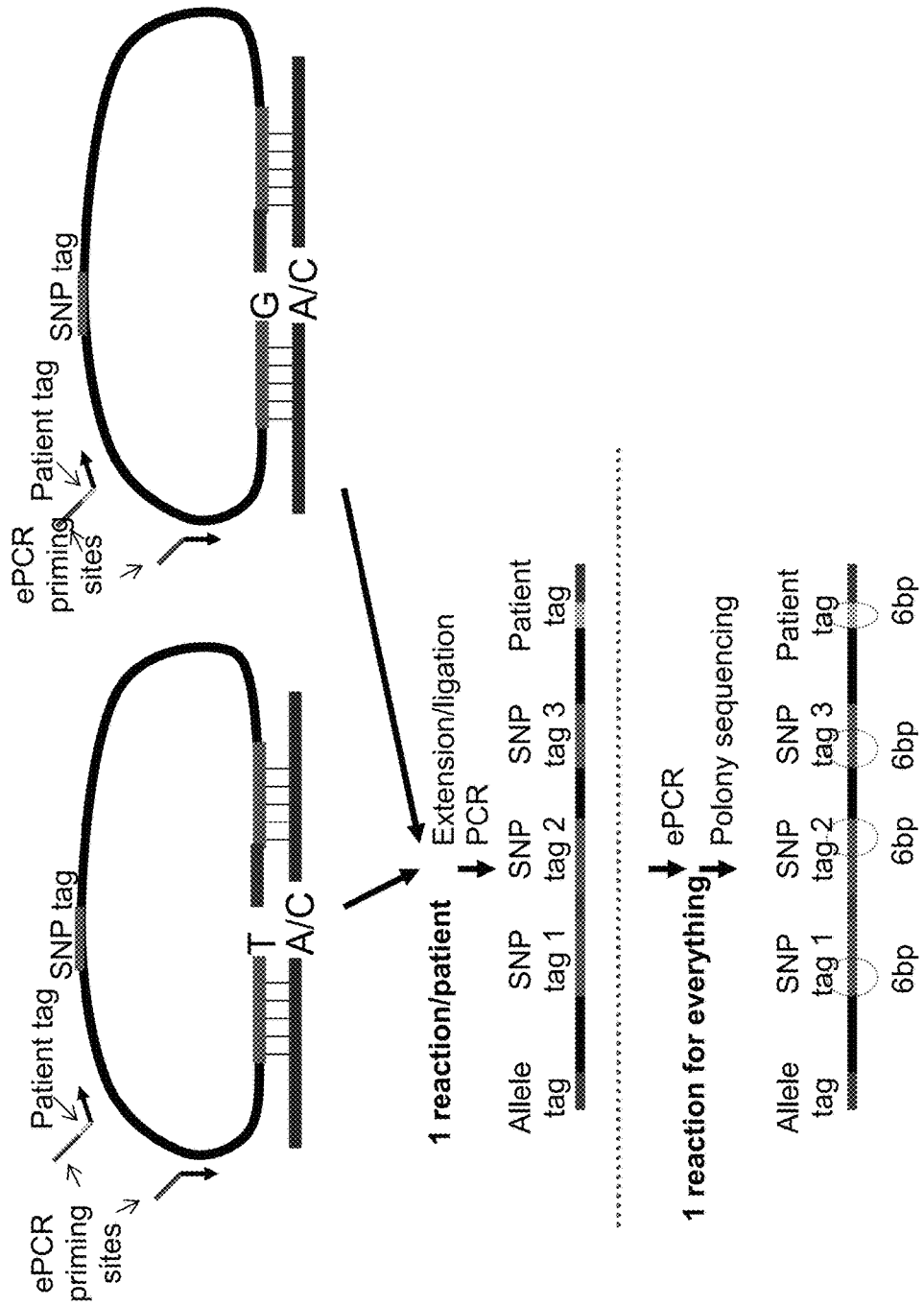
FIG. 2 schematically depicts an alternate use of two molecular inversion probes.

FIG. 2 is a schematic showing an alternate use of two molecular inversion probes. The probes each include two ePCR priming sites, an allele tag, a patient tag and an optional SNP tag. The gap between each probe is greater than one nucleotide. The gap can be 2, 3, 4, 5, 6, 7, 8, 9, or 10 or more nucleotides in length. The gap is filled by the appropriate number and type of nucleotides.

The experimental design shown in FIG. 2 provides the advantages of very simple assays that can handle many (e.g., on the order of millions) of SNPs in hundreds of patients using a single assay. This experimental design further provides the advantage of the ability to use various gap lengths. Two probes are used for each loci. The specificity for the experimental design shown in FIG. 2 may not be as high as for the experimental design shown in FIG. 1, and the variant site is not queried directly.

According to one aspect of the present invention, methods are provided whereby tags are separate from the point of ligation in the probe. A different tag or pair of tags is provided for each combination of location in the genome and allele. Allele detection is accomplished either (1) by making the ligation dependent on the efficient polymerase filling-in with one specific dNTP in the gap as described by Hardenbol cited previously or filling in the gap with multiple dNTPs if the gap is larger than one base or (2) by utilizing the specificity of the ligation reaction itself. According to one embodiment, multiple DNA sources per amplification and sequencing pool are provided. After the gap filling step, a type IIS endonuclease cut (guided from a binding site as close as possible to the filled-gap) is ligated to a known sequence tag which can contain base pairs which identify the sample (e.g. the patient) with at least 1 bp per each 4 samples. More than 1 bp per 4 samples can be used if error reduction via redundant encoding is desired. Alternatively, separate MIP pools can be made with different tags built in. This provides the advantage of saving the type IIS cleavage and bimolecular ligation steps, but also requires more pools of MIP single stranded DNA.

An alternate embodiment of the present invention is directed to enriching probe pools for shotgun sequencing. Various regions around the genome (e.g. exons, SNPs, mutable regions like CGs, and/or highly conserved regions) are amplified. A large pool of these amplified regions is released from the MIP backbone part of the circular probes by type IIS restriction enzymes or dU or rU methods. Preferably for this method, some degree of degeneracy or randomness in the primer sequences is advantageous.

A further alternate embodiment of the present invention includes shareable probe pools. According to this aspect large quantities and diverse numbers of MIP probes on oligonucleotide chips (e.g. Agilent) are made and in a way that is poolable & amplifiable (and hence easily shared). Each MIP oligo is flanked by universal oligos for amplification which can be removed. The following approaches are used to isolate the appropriate strand of the double stranded PCR products as well as to remove the universal primer regions mentioned above. (1) using one or more 3' phosphothioate nucleotides on one of the two primers, (2) using exonucleases sensitive to 3' or 5' overhang (or lack thereof). One primer has one or more dU and can be removed by USER (which is a mixture of uracil DNA glycosylase and DNA glycosylase-lyase Endonuclease VIII) then the other primer has rU which can be cleaved by alkali. (3) using solid phase immobilization (e.g. magnetic bead streptavidin) of one primer with selective release of the other strand using alkali or heat to melt the base-pairs. (4) using asymmetric PCR (using an excess of the desired strand's primer) and (5) using separation by size and/or electrophoretic differences of the two strands by engineering the oligos to have different lengths (either by use of the rU or dU methods or 2'O methyl groups to block PCR extension beyond the 2'Ome.

Embodiments of the present invention are useful in analyzing RNA for allele specific quantitation. The above methods when applied to RNA have the advantages of maintaining any differences in ratio between the two allelic RNA levels (Yan et al. (2002) *Science* 297:1143) while evening out the huge difference in RNA levels in going from gene to gene, effectively normalizing to the plateau levels set by the levels of the input MIP single-stranded DNA.

Embodiments of the present invention also find particular application to synthetic genes and genomes, for example to assist in synthetic multiplexing in amplification, error correction and/or assembly as described by Tian et al. (2004) *Nature* 432:1050.

Embodiments of the present invention are directed to the use of MIP technology with polony sequencing technology or synthetic genomic technology. Polony technology is described in U.S. Pat. Nos. 6,432,360, 6,485,944 and 6,511,803 and PCT/US05/06425. In general, the term "polony" refers to "polymerized colony." Polony technology relates to the amplification of nucleic acids. In general, a pool of nucleic acids is provided, preferably in an array where the nucleic acids are immobilized to a support. The nucleic acids are randomly patterned on the support. The nucleic acids are then amplified in situ to produce colonies of polymerized nucleic acids. Polony amplification can also take place on beads where a nucleic acid is attached to a bead and then polymerized in situ.

There are many hybridization-based assays that comprise a hybridization step that forms a structure or complex with a target polynucleotide, such as a fragment of genomic DNA, and an enzymatic processing step in which one or more enzymes either recognize such structure or complex as a substrate or are prevented from recognizing a substrate because it is protected by such structure or complex. In particular, such assays are widely used in multiplexed formats to simultaneously analyze DNA samples at multiple loci, e.g. allele-specific multiplex PCR, arrayed primer extension (APEX) technology, solution phase primer extension or ligation assays, and the like, described in the following exemplary references: Syvanen, *Nature Genetics Supplement*, 37: S5-S10 (2005); Shumaker et al., *Hum. Mut.*, 7: 346-354 (1996); Huang et al., U.S. Pat. Nos. 6,709,816 and 6,287,778; Fan et al., U.S. patent publication 2003/0003490; Gunderson et al., U.S. patent publication 2005/0037393; Hardenbol et al., *Nature Biotechnology*, 21: 673-678 (2003); Nilsson et al., *Science*, 265: 2085-2088 (1994); Baner et al., *Nucleic Acids Research*, 26: 5073-5078 (1998); Lizardi et al., *Nat. Genet.*, 19: 225-232 (1998); Gerry et al., *J. Mol. Biol.*, 292: 251-262 (1999); Fan et al., *Genome Research*, 10: 853-860 (2000); International patent publications WO 2002/57491 and WO 2000/58516; U.S. Pat. Nos. 6,506,594 and 4,883,750; and the like.

In one aspect, hybridization-based assays include circularizing probes, such as padlock probes, rolling circle probes, molecular inversion probes, linear amplification molecules for multiplexed PCR, and the like, e.g. padlock probes being disclosed in U.S. Pat. Nos. 5,871,921; 6,235,472; 5,866,337; and Japanese patent JP. 4-262799; rolling circle probes being disclosed in Aono et al., JP-4-262799; Lizardi, U.S. Pat. Nos. 5,854,033; 6,183,960; 6,344,239; molecular inversion probes being disclosed in Hardenbol et al. (supra) and in Willis et al., U.S. Pat. No. 6,858,412; and linear amplification molecules being disclosed in Faham et al., U.S. patent publication 2003/0104459. Such probes are desirable because non-circularized probes can be digested with single stranded exonucleases thereby greatly reducing background noise due to spurious amplifications, and the like. In the case of molecular inversion probes (MIPs), padlock probes, and rolling circle probes, constructs for generating labeled target sequences are formed by circularizing a linear version of the probe in a template-driven reaction on a target polynucleotide followed by digestion of non-circularized polynucleotides in the reaction mixture, such as target polynucleotides, unligated probe, probe concatemers, and the like, with an exonuclease, such as exonuclease I.

Methods of conducting multiplexed hybridization-based assays using microarrays, and like platforms, suitable for the present invention are well known in the art. Guidance for selecting conditions and materials for applying labeled sequences to solid phase supports, such as microarrays, may be found in the literature, e.g. Wetmur, *Crit. Rev. Biochem. Mol. Biol.*, 26: 227-259 (1991); DeRisi et al., *Science*, 278: 680-686 (1997); Chee et al., *Science*, 274: 610-614 (1996); Duggan et al., *Nature Genetics*, 21: 10-14 (1999); Schena, Editor, *Microarrays: A Practical Approach* (IRL Press, Washington, 2000); Freeman et al., *Biotechniques*, 29: 1042-1055 (2000); and like references. Methods and apparatus for carrying out repeated and controlled hybridization reactions have been described in U.S. Pat. Nos. 5,871,928, 5,874,219, 6,045,996 and 6,386,749, 6,391,623. Hybridization conditions typically include salt concentrations of less than about IM, more usually less than about 500 mM and less than about 200 mM. Hybridization temperatures can be as low as 5° C., but are typically greater than 22° C., more typically greater than about 30° C., and preferably in excess of about 37° C. Hybridizations are usually performed under stringent conditions, i.e., conditions under which a probe will stably hybridize to a perfectly complementary target sequence, but will not stably hybridize to sequences that have one or more mismatches. The stringency of hybridization conditions depends on several factors, such as probe sequence, probe length, temperature, salt concentration, concentration of organic solvents, such as formamide, and the like. How such factors are selected is usually a matter of design choice to one of ordinary skill in the art for any particular embodiment. Usually, stringent conditions are selected to be about 5° C. lower than the $T_m$ for the specific sequence for particular ionic strength and pH. Exemplary hybridization conditions include salt concentration of at least 0.01 M to about 1 M Na ion concentration (or other salts) at a pH 7.0 to 8.3 and a temperature of at least 25° C. Additional exemplary hybridization conditions include the following: 5×SSPE (750 mM NaCl, 50 mM sodium phosphate, 5 mM EDTA, pH 7.4).

Exemplary hybridization procedures for applying labeled target sequence to a GENFLEX™ microarray (Affymetrix, Santa Clara, Calif.) is as follows: denatured labeled target sequence at 95-100° C. for 10 minutes and snap cool on ice for 2-5 minutes. The microarray is pre-hybridized with 6×SSPE-T (0.9 M NaCl 60 mM $NaH_2$, $PO_4$, 6 mM EDTA (pH 7.4), 0.005% Triton X-100) +0.5 mg/ml of BSA for a few minutes, then hybridized with 120 μL hybridization solution (as described below) at 42° C. for 2 hours on a rotisserie at 40 RPM. Hybridization Solution consists of 3M TMACL (tetramethylammonium chloride), 50 mM MES ((2-[N-Morpholino]ethanesulfonic acid) Sodium Salt) (pH 6.7), 0.01% of Triton X-100, 0.1 mg/ml of herring sperm DNA, optionally 50 pM of fluorescein-labeled control oligonucleotide, 0.5 mg/ml of BSA (Sigma) and labeled target sequences in a total reaction volume of about 120 μL. The microarray is rinsed twice with 1×SSPE-T for about 10 seconds at room temperature, then washed with 1×SSPE-T for 15-20 minutes at 40° C. on a rotisserie at 40 RPM. The microarray is then washed 10 times with 6×SSPE-T at 22° C. on a fluidic station (e.g. model FS400, Affymetrix, Santa Clara, Calif.). Further processing steps may be required depending on the nature of the label(s) employed, e.g. direct or indirect. Microarrays containing labeled target sequences may be scanned on a confocal scanner (such as available commercially from Affymetrix) with a resolution of 60-70 pixels per feature and filters and other settings as appropriate for the labels employed. GENECHIP® (Affymetrix) or similar software may be used to convert the image files into digitized files for further data analysis.

Samples or specimens containing target polynucleotides, such as fragments of genomic DNA, may come from a wide variety of sources for use with the present invention, including, but not limited to, cell cultures, animal or plant tissues, patient biopsies, environmental samples, and the like. Samples are prepared for assays of the invention using conventional techniques, which typically depend on the source from which a sample or specimen is taken.

Prior to carrying out reactions on a sample, it will often be desirable to perform one or more ample preparation operations upon the sample. Typically, these sample preparation operations will include such manipulations as extraction of intracellular material, e.g., nucleic acids from whole cell samples, viruses and the like.

For those embodiments where whole cells, viruses or other tissue samples are being analyzed, it will typically be necessary to extract the nucleic acids from the cells or viruses, prior to continuing with the various sample preparation operations. Accordingly, following sample collection, nucleic acids may be liberated from the collected cells, viral coat, etc., into a crude extract, followed by additional treatments to prepare the sample for subsequent operations, e.g., denaturation of contaminating (DNA binding) proteins, purification, filtration, desalting, and the like. Liberation of nucleic acids from the sample cells or viruses, and denaturation of DNA binding proteins may generally be performed by chemical, physical, or electrolytic lysis methods. For example, chemical methods generally employ lysing agents to disrupt the cells and extract the nucleic acids from the cells, followed by treatment of the extract with chaotropic salts such as guanidinium isothiocyanate or urea to denature any contaminating and potentially interfering proteins. Generally, where chemical extraction and/or denaturation methods are used, the appropriate reagents may be incorporated within a sample preparation chamber, a separate accessible chamber, or may be externally introduced.

Following extraction, it will often be desirable to separate the nucleic acids from other elements of the crude extract, e.g., denatured proteins, cell membrane particles, salts, and the like. Removal of particulate matter is generally accomplished by filtration, flocculation or the like. A variety of filter types may be readily incorporated into the device. Further, where chemical denaturing methods are used, it may be desirable to desalt the sample prior to proceeding to the next step. Desalting of the sample, and isolation of the nucleic acid may generally be carried out in a single step, e.g., by binding the nucleic acids to a solid phase and washing away the contaminating salts or performing gel filtration chromatography on the sample, passing salts through dialysis membranes, and the like. Suitable solid supports for nucleic acid binding include, e.g., diatomaceous earth, silica (i.e., glass wool), or the like. Suitable gel exclusion media, also well known in the art, may also be readily incorporated into the devices of the present invention, and is commercially available from, e.g., Pharmacia and Sigma Chemical.

In some applications, such as measuring target polynucleotides in rare cells from a patient's blood, an enrichment step may be carried out prior to conducting an assay, such as by immunomagnetic isolation, fluorescent cell sorting or other such technique. Such isolation or enrichment may be carried out using a variety of techniques and materials known in the art, as disclosed in the following representative references: Terstappen et al., U.S. Pat. No. 6,365,362; Terstappen et al., U.S. Pat. No. 5,646,001; Rohr et al., U.S. Pat. No. 5,998, 224; Kausch et al., U.S. Pat. No. 5,665,582; Kresse et al., U.S. Pat. No. 6,048,515; Kausch et al., U.S. Pat. No. 5,508,164; Miltenyi et al., U.S. Pat. No. 5,691,208; Molday, U.S. Pat. No. 4,452,773; Kronick, U.S. Pat. No. 4,375,407; Radbruch et al., Chapter 23, in *Methods in Cell Biology*, Vol. 42 (Academic Press, New York, 1994); Uhlen et al., *Advances in Biomagnetic Separation* (Eaton Publishing, Natick, 1994); Safarik et al., *J. Chromatography B*, 722: 33-53 (1999); Miltenyi et al., *Cytometry*, 11: 231-238 (1990); Nakamura et al., *Biotechnol. Prog.*, 17: 1145-1155 (2001); Moreno et al., *Urology*, 58: 386-392 (2001); Racila et al., *Proc. Natl. Acad. Sci.*, 95: 4589-4594 (1998); Zigeuner et al., *J. Urology*, 169: 701-705 (2003); Ghossein et al., *Seminars in Surgical Oncology*, 20: 304-311 (2001).

In one aspect, genomic DNA for analysis is obtained using standard commercially available DNA extraction kits, e.g., PUREGENE® DNA Isolation Kit (Gentra Systems, Minneapolis, Minn.). In another aspect, for assaying human genomic DNA with a multiplex hybridization-based assay containing from about 1000 to 50,000 probes, a DNA sample may be used having an amount within the range of from about 200 ng to about 1 microgram. When sample material is scarce, prior to assaying, sample DNA may be amplified by whole genome amplification, or like technique, to increase the total amount of DNA available for assaying. Several whole genome, or partial genome, amplification techniques are known in the art, such as the following: Telenius et al. (1992) *Genomics* 13:718; Cheung et al. (1996) *Proc. Natl. Acad. Sci. U.S.A.* 93:14676; Dean et al. (2001) *Genome Research* 11:1095; U.S. Pat. Nos. 6,124, 120; 6,280,949; 6,617,137; and the like.

Terms and symbols of nucleic acid chemistry, biochemistry, genetics, and molecular biology used herein follow those of standard treatises and texts in the field, e.g., Komberg and Baker, *DNA* Replication, Second Edition (W.H. Freeman, New York, 1992); Lehninger, *Biochemistry*, Second Edition (Worth Publishers, New York, 1975); Strachan and Read, *Human Molecular Genetics*, Second Edition (Wiley-Liss, New York, 1999); Eckstein, editor, *Oligonucleotides and Analogs: A Practical Approach* (Oxford University Press, New York, 1991); Gait, editor, *Oligonucleotide Synthesis: A Practical Approach* (IRL Press, Oxford, 1984); and the like.

"Addressable" or "addressed" in reference to tag complements means that the nucleotide sequence, or perhaps other physical or chemical characteristics, of a tag complement can be determined from its address, i.e., a one-to-one correspondence between the sequence or other property of the tag complement and a spatial location on, or characteristic of, the solid phase support to which it is attached. In certain aspects, an address of a tag complement is a spatial location, e.g., the planar coordinates of a particular region containing copies of the tag complement. In other embodiments, probes may be addressed in other ways, e.g., by microparticle size, shape, color, color ratio or fluorescent ratio, radio frequency of micro-transponder, or the like, e.g., Kettman et al. (1998) *Cytometry* 33:234; Xu et al. (2003) *Nucl. Acids Res.* 31:e43; Bruchez Jr. et al., U.S. Pat. No. 6,500,622; Mandecki, U.S. Pat. No. 6,376,187; Stuelpnagel et al., U.S. Pat. No. 6,396,995; Chee et al., U.S. Pat. No. 6,544,732; Chandler et al., PCT publication WO 97/14028; and the like. According to the present invention, such terms also may refer to a nucleotide sequence that specifically identifies DNA or RNA sequences as having been captured from a given patient or other subject.

"Amplicon" means the product of a polynucleotide amplification reaction. That is, it is a population of polynucleotides, usually double stranded, that are replicated from one or more starting sequences. The one or more starting sequences may be one or more copies of the same sequence, or it may be a mixture of different sequences. Amplicons may be produced by a variety of amplification reactions whose products are multiple replicates of one or more target nucleic acids. Generally, amplification reactions producing amplicons are "template-driven" in that base pairing of reactants, either nucleotides or oligonucleotides, have complements in a template polynucleotide that are required for the creation of reaction products. In one aspect, template-driven reactions are primer extensions with a nucleic acid polymerase or oligonucleotide ligations with a nucleic acid ligase. Such reactions include, but are not limited to, polymerase chain reaction (PCR), linear polymerase reactions, nucleic acid sequence-based amplification (NASBA), rolling circle amplifications, and the like, disclosed in the following references: Mullis et al., U.S. Pat. Nos. 4,683,195; 4,965,188; 4,683,202; 4,800,159 (PCR); Gelfand et al., U.S. Pat. No. 5,210,015 (real-time PCR with "Taqman" probes); Wittwer et al., U.S. Pat. No. 6,174,670; Kacian et al., U.S. Pat. No. 5,399,491 ("NASBA"); Lizardi, U.S. Pat. No. 5,854,033; Aono et al., Japanese Patent Pub. JP 4-262799 (rolling circle amplification); and the like. In one aspect, amplicons of the invention are produced by PCR. An amplification reaction may be a "real-time" amplification if a detection chemistry is available that permits a reaction product to be measured as the amplification reaction progresses, e.g. "real-time PCR" described below, or "real-time NASBA" as described in Leone et al. (1998) *Nucl. Acids Res.* 26:2150, and like references. As used herein, the term "amplifying" means performing an amplification reaction. A "reaction mixture" means a solution containing all the necessary reactants for performing a reaction, which may include, but not be limited to, buffering agents to maintain pH at a selected level during a reaction, salts, co-factors, scavengers, and the like. Methods of "polony amplification" are also described in U.S. Pat. No. 6,432,360, U.S. Pat. No. 6,511,803 and U.S. Pat. No. 6,485,944.

"Complementary" or "substantially complementary" refers to the hybridization or base pairing or the formation of a duplex between nucleotides or nucleic acids, such as, for instance, between the two strands of a double stranded DNA molecule or between an oligonucleotide primer and a primer binding site on a single stranded nucleic acid. Complementary nucleotides are, generally, A and T (or A and U), or C and G. Two single-stranded RNA or DNA molecules are said to be substantially complementary when the nucleotides of one strand, optimally aligned and compared and with appropriate nucleotide insertions or deletions, pair with at least about 80% of the nucleotides of the other strand, usually at least about 90% to 95%, and more preferably from about 98 to 100%. Alternatively, substantial complementarity exists when an RNA or DNA strand will hybridize under selective hybridization conditions to its complement. Typically, selective hybridization will occur when there is at least about 65% complementary over a stretch of at least 14 to 25 nucleotides, preferably at least about 75%, more preferably at least about 90% complementary. See Kanehisa (1984) *Nucl. Acids Res.* 12:203. According to the present invention, useful MIP primer sequences hybridize to sequences that flank the nucleotide base or series of bases to be captured.

"Complex" means an assemblage or aggregate of molecules in direct or indirect contact with one another. In one aspect, "contact," or more particularly, "direct contact," in reference to a complex of molecules or in reference to specificity or specific binding, means two or more molecules are close enough so that attractive noncovalent interactions, such as van der Waal forces, hydrogen bonding, ionic and hydrophobic interactions, and the like, dominate the interaction of the molecules. In such an aspect, a complex of molecules is stable in that under assay conditions the complex is thermodynamically more favorable than a non-aggregated, or non-complexed, state of its component molecules. As used herein, "complex" refers to a duplex or triplex of polynucleotides or a stable aggregate of two or more proteins. In regard to the latter, a complex is formed by an antibody specifically binding to its corresponding antigen.

"Duplex" means at least two oligonucleotides and/or polynucleotides that are fully or partially complementary undergo Watson-Crick type base pairing among all or most of their nucleotides so that a stable complex is formed. The terms "annealing" and "hybridization" are used interchangeably to mean the formation of a stable duplex. In one aspect, stable duplex means that a duplex structure is not destroyed by a stringent wash, e.g., conditions including temperature of about 5° C. less that the $T_m$ of a strand of the duplex and low monovalent salt concentration, e.g., less than 0.2 M, or less than 0.1 M. "Perfectly matched" in reference to a duplex means that the polynucleotide or oligonucleotide strands making up the duplex form a double stranded structure with one another such that every nucleotide in each strand undergoes Watson-Crick base pairing with a nucleotide in the other strand. The term "duplex" comprehends the pairing of nucleoside analogs, such as deoxyinosine, nucleosides with 2-aminopurine bases, PNAs, and the like, that may be employed. A "mismatch" in a duplex between two oligonucleotides or polynucleotides means that a pair of nucleotides in the duplex fails to undergo Watson-Crick bonding.

"Genetic locus," or "locus" in reference to a genome or target polynucleotide, means a contiguous subregion or segment of the genome or target polynucleotide. As used herein, genetic locus, or locus, may refer to the position of a nucleotide, a gene, or a portion of a gene in a genome, including mitochondrial DNA, or it may refer to any contiguous portion of genomic sequence whether or not it is within, or associated with, a gene. In one aspect, a genetic locus refers to any portion of genomic sequence, including mitochondrial DNA, from a single nucleotide to a segment of few hundred nucleotides, e.g. 100-300, in length. Usually, a particular genetic locus may be identified by its nucleotide sequence, or the nucleotide sequence, or sequences, of one or both adjacent or flanking regions. In another aspect, a genetic locus refers to the expressed nucleic acid product of a gene, such as an RNA molecule or a cDNA copy thereof.

"Hybridization" refers to the process in which two single-stranded polynucleotides bind noncovalently to form a stable double-stranded polynucleotide. The term "hybridization" may also refer to triple-stranded hybridization. The resulting (usually) double-stranded polynucleotide is a "hybrid" or "duplex." "Hybridization conditions" will typically include salt concentrations of less than about 1 M, more usually less than about 500 mM and even more usually less than about 200 mM. Hybridization temperatures can be as low as 5° C., but are typically greater than 22° C., more typically greater than about 30° C., and often in excess of about 37° C. Hybridizations are usually performed under stringent conditions, i.e., conditions under which a probe will hybridize to its target subsequence. Stringent conditions are sequence-dependent and are different in different circumstances. Longer fragments may require higher hybridization temperatures for specific hybridization. As other factors may affect the stringency of hybridization, including base composition and length of the complementary strands, presence of organic solvents and extent of base mismatching, the combination of parameters is more important than the absolute measure of any one alone. Generally, stringent conditions are selected to be about 5° C. lower than the $T_m$ for the specific sequence at s defined ionic strength and pH. Exemplary stringent conditions include salt concentration of at least 0.01 M to no more than 1 M Na ion concentration (or other salts) at a pH 7.0 to 8.3 and a temperature of at least 25° C. For example, conditions of 5×SSPE (750 mM NaCl, 50 mM Na phosphate, 5 mM EDTA, pH 7.4) and a temperature of 25-30° C. are suitable for allele-specific probe hybridizations. For stringent conditions, see for example, Sambrook, Fritsche and Maniatis, *Molecular Cloning A Laboratory Manual*, 2nd Ed. Cold Spring Harbor Press (1989) and Anderson *Nucleic Acid Hybridization*, 1$^{st}$ Ed., BIOS Scientific Publishers Limited (1999). "Hybridizing specifically to" or "specifically hybridizing to" or like expressions refer to the binding, duplexing, or hybridizing of a molecule substantially to or only to a particular nucleotide sequence or sequences under stringent conditions when that sequence is present in a complex mixture (e.g., total cellular) DNA or RNA.

"Hybridization-based assay" means any assay that relies on the formation of a stable complex as the result of a specific binding event. In one aspect, a hybridization-based assay means any assay that relies on the formation of a stable duplex or triplex between a probe and a target nucleotide sequence for detecting or measuring such a sequence. In one aspect, probes of such assays anneal to (or form duplexes with) regions of target sequences in the range of from 8 to 100 nucleotides; or in other aspects, they anneal to target sequences in the range of from 8 to 40 nucleotides, or more usually, in the range of from 8 to 20 nucleotides. A "probe" in reference to a hybridization-based assay means a polynucleotide that has a sequence that is capable of forming a stable hybrid (or triplex) with its complement in a target nucleic acid and that is capable of being detected, either directly or indirectly. Hybridization-based assays include, without limitation, assays that use the specific base-pairing of one or more oligonucleotides as target recognition components, such as polymerase chain reactions, NASBA reactions, oligonucleotide ligation reactions, single-base extension reactions, circularizable probe reactions, allele-specific oligonucleotide hybridizations, either in solution phase or bound to solid phase supports, such as microarrays or microbeads, and the like. An important subset of hybridization-based assays include such assays that have at least one enzymatic processing step after a hybridization step. Hybridization-based assays of this subset include, without limitation, polymerase chain reactions, NASBA reactions, oligonucleotide ligation reactions, cleavase reactions, e.g., in INVADER™ assays, single-base extension reactions, probe circularization reactions, and the like. There is extensive guidance in the literature on hybridization-based assays, e.g., Hames et al., editors, *Nucleic Acid Hybridization a Practical Approach* (IRL Press, Oxford, 1985); Tijssen, *Hybridization with Nucleic Acid Probes*, Parts I & II (Elsevier Publishing Company, 1993); Hardiman, *Microarray Methods and Applications* (DNA Press, 2003); Schena, editor, *DNA Microarrays a Practical Approach* (IRL Press, Oxford, 1999); and the like. In one aspect, hybridization-based assays are solution phase assays; that is, both probes and target sequences hybridize under conditions that are substantially free of surface effects or influences on reaction rate. A solution phase assay includes circumstances where either probes or target sequences are attached to microbeads such that the attached sequences have substantially the same environment (e.g., permitting reagent access, etc.) as free sequences. In another aspect, hybridization-based assays include immunoassays wherein antibodies employ nucleic acid reporters based on amplification. In such assays, antibody probes specifically bind to target molecules, such as proteins, in separate reactions, after which the products of such reactions (i.e., antibody-protein complexes) are combined and nucleic acid reporters are amplified. Preferably, such nucleic acid reporters include oligonucleotide tags that are converted enzymatically into labeled oligonucleotide tags for analysis on a microarray, as described below. The following exemplary references disclose antibody-nucleic acid conjugates for immunoassays: Baez et al., U.S. Pat. No. 6,511,809; Sano et al., U.S. Pat. No. 5,665,539; Eberwine et al., U.S. Pat. No. 5,922,553; Landegren et al., U.S. Pat. No. 6,558,928; Landegren et al., U.S. Patent Pub. 2002/0064779; and the like. In particular, the two latter patent publications by Landegren et al. disclose steps of forming amplifiable probes after a specific binding event.

"Kit" refers to any delivery system for delivering materials or reagents for carrying out a method of the invention. In the context of assays, such delivery systems include systems that allow for the storage, transport, or delivery of reaction reagents (e.g., probes, enzymes, etc. in the appropriate containers) and/or supporting materials (e.g., buffers, written instructions for performing the assay etc.) from one location to another. For example, kits include one or more enclosures (e.g., boxes) containing the relevant reaction reagents and/or supporting materials for assays of the invention. In one aspect, kits of the invention comprise probes specific for polymorphic loci. In another aspect, kits comprise nucleic acid standards for validating the performance of probes specific for polymorphic loci. Such contents may be delivered to the intended recipient together or separately. For example, a first container may contain an enzyme for use in an assay, while a second container contains probes.

"Ligation" means to form a covalent bond or linkage between the termini of two or more nucleic acids, e.g., oligonucleotides and/or polynucleotides, in a template-driven reaction. The nature of the bond or linkage may vary widely and the ligation may be carried out enzymatically or chemically. As used herein, ligations are usually carried out enzymatically to form a phosphodiester linkage between a 5' carbon of a terminal nucleotide of one oligonucleotide with 3' carbon of another oligonucleotide. A variety of template-driven ligation reactions are described in the following references: Whitely et al., U.S. Pat. No. 4,883,750; Letsinger et al., U.S. Pat. No. 5,476,930; Fung et al., U.S. Pat. No. 5,593,826; Kool, U.S. Pat. No. 5,426,180; Landegren et al., U.S. Pat. No. 5,871,921; Xu and Kool (1999) *Nucl. Acids Res.* 27:875; Higgins et al., *Meth. in Enzymol.* (1979) 68:50; Engler et al. (1982) *The Enzymes,* 15:3 (1982); and Namsaraev, U.S. Patent Pub. 2004/0110213.

"Microarray" refers in one embodiment to a type of multiplex assay product that comprises a solid phase support having a substantially planar surface on which there is an array of spatially defined non-overlapping regions or sites that each contain an immobilized hybridization probe. "Substantially planar" means that features or objects of interest, such as probe sites, on a surface may occupy a volume that extends above or below a surface and whose dimensions are small relative to the dimensions of the surface. For example, beads disposed on the face of a fiber optic bundle create a substantially planar surface of probe sites, or oligonucleotides disposed or synthesized on a porous planar substrate creates a substantially planar surface. Spatially defined sites may additionally be "addressable" in that its location and the identity of the immobilized probe at that location are known or determinable. Probes immobilized on microarrays include nucleic acids, such as oligonucleotide barcodes, that are generated in or from an assay reaction. Typically, the oligonucleotides or polynucleotides on microarrays are single stranded and are covalently attached to the solid phase support, usually by a 5'-end or a 3'-end. The density of non-overlapping regions containing nucleic acids in a microarray is typically greater than 100 per $cm^2$, and more preferably, greater than 1000 per $cm^2$. Microarray technology relating to nucleic acid probes is reviewed in the following exemplary references: Schena, Editor, *Microarrays: A Practical Approach* (IRL Press, Oxford, 2000); Southern, *Current Opin. Chem. Biol.,* 2: 404-410 (1998); *Nature Genetics* Supplement, 21:1-60 (1999); and Fodor et al., U.S. Pat. Nos. 5,424,186; 5,445,934; and 5,744,305. A microarray may comprise arrays of microbeads, or other microparticles, alone or disposed on a planar surface or in wells or other physical configurations that can be sued to separate the beads. Such microarrays may be formed in a variety of ways, as disclosed in the following exemplary references: Brenner et al. (2000) *Nat. Biotechnol.* 18:630; Tulley et al., U.S. Pat. No. 6,133,043; Stuelpnagel et al., U.S. Pat. No. 6,396,995; Chee et al., U.S. Pat. No. 6,544,732; and the like. In one format, microarrays are formed by randomly disposing microbeads having attached oligonucleotides on a surface followed by determination of which microbead carries which oligonucleotide by a decoding procedure, e.g. as disclosed by Gunderson et al., U.S. Patent Pub. No. 2003/0096239.

"Microarrays" or "arrays" can also refer to a heterogeneous pool of nucleic acid molecules that is distributed over a support matrix. The nucleic acids can be covalently or noncovalently attached to the support. Preferably, the nucleic acid molecules are spaced at a distance from one another sufficient to permit the identification of discrete features of the array. Nucleic acids on the array may be non-overlapping or partially overlapping. Methods of transferring a nucleic acid pool to support media is described in U.S. Pat. No. 6,432,360. Bead based methods useful in the present invention are disclosed in PCT US05/04373.

"Amplifying" includes the production of copies of a nucleic acid molecule of the array or a nucleic acid molecule bound to a bead via repeated rounds of primed enzymatic synthesis. "In situ" amplification indicated that the amplification takes place with the template nucleic acid molecule positioned on a support or a bead, rather than in solution. In situ amplification methods are described in U.S. Pat. No. 6,432,360.

"Support" can refer to a matrix upon which nucleic acid molecules of a nucleic acid array are placed. The support can be solid or semi-solid or a gel. "Semi-solid" refers to a compressible matrix with both a solid and a liquid component, wherein the liquid occupies pores, spaces or other interstices between the solid matrix elements. Semi-solid supports can be selected from polyacrylamide, cellulose, polyamide (nylon) and crossed linked agarose, dextran and polyethylene glycol.

"Randomly-patterned" or "random" refers to non-ordered, non-Cartesian distribution (in other words, not arranged at pre-determined points along the x- or y-axes of a grid or at defined "clock positions," degrees or radii from the center of a radial pattern) of nucleic acid molecules over a support, that is not achieved through an intentional design (or program by which such design may be achieved) or by placement of individual nucleic acid features. Such a "randomly-patterned" or "random" array of nucleic acids may be achieved by dropping, spraying, plating or spreading a solution, emulsion, aerosol, vapor or dry preparation comprising a pool of nucleic acid molecules onto a support and allowing the nucleic acid molecules to settle onto the support without intervention in any manner to direct them to specific sites thereon. Arrays of the invention can be randomly patterned or random.

"Heterogeneous" refers to a population or collection of nucleic acid molecules that comprises a plurality of different sequences. According to one aspect, a heterogeneous pool of nucleic acid molecules results from a preparation of RNA or DNA from a cell which may be unfractionated or partially-fractionated.

"Nucleoside" as used herein includes the natural nucleosides, including 2'-deoxy and 2'-hydroxyl forms, e.g. as described in Komberg and Baker, *DNA Replication,* 2nd Ed. (Freeman, San Francisco, 1992). "Analogs" in reference to nucleosides includes synthetic nucleosides having modified base moieties and/or modified sugar moieties, e.g., described by Scheit, *Nucleotide Analogs* (John Wiley, New York, 1980); Uhlman and Peyman, *Chemical Reviews,* 90:543-584 (1990), or the like, with the proviso that they are capable of specific hybridization. Such analogs include synthetic nucleosides designed to enhance binding properties, reduce complexity, increase specificity, and the like. Polynucleotides comprising analogs with enhanced hybridization or nuclease resistance properties are described in Uhlman and Peyman (cited above); Crooke et al., *Exp. Opin. Ther. Patents*, 6: 855-870 (1996); Mesmaeker et al., *Current Opinion in Structural Biology*, 5:343-355 (1995); and the like. Exemplary types of polynucleotides that are capable of enhancing duplex stability include oligonucleotide phosphoramidates (referred to herein as "amidates"), peptide nucleic acids (referred to herein as "PNAs"), oligo-2'-O-alkylribonucleotides, polynucleotides containing C-5 propynylpyrimidines, locked nucleic acids (LNAs), and like compounds. Such oligonucleotides are either available commercially or may be synthesized using methods described in the literature.

"Oligonucleotide" or "polynucleotide," which are used synonymously, means a linear polymer of natural or modified nucleosidic monomers linked by phosphodiester bonds or analogs thereof. The term "oligonucleotide" usually refers to a shorter polymer, e.g., comprising from about 3 to about 100 monomers, and the term "polynucleotide" usually refers to longer polymers, e.g., comprising from about 100 monomers to many thousands of monomers, e.g., 10,000 monomers, or more. Oligonucleotides comprising probes or primers usually have lengths in the range of from 12 to 60 nucleotides, and more usually, from 18 to 40 nucleotides. Oligonucleotides and polynucleotides may be natural or synthetic. Oligonucleotides and polynucleotides include deoxyribonucleosides, ribonucleosides, and non-natural analogs thereof, such as anomeric forms thereof, peptide nucleic acids (PNAs), and the like, provided that they are capable of specifically binding to a target genome by way of a regular pattern of monomer-to-monomer interactions, such as Watson-Crick type of base pairing, base stacking, Hoogsteen or reverse Hoogsteen types of base pairing, or the like.

Usually nucleosidic monomers are linked by phosphodiester bonds. Whenever an oligonucleotide is represented by a sequence of letters, such as "ATGCCTG," it will be understood that the nucleotides are in 5' to 3' order from left to right and that "A" denotes deoxyadenosine, "C" denotes deoxycytidine, "G" denotes deoxyguanosine, "T" denotes deoxythymidine, and "U" denotes the ribonucleoside, uridine, unless otherwise noted. Usually oligonucleotides comprise the four natural deoxynucleotides; however, they may also comprise ribonucleosides or non-natural nucleotide analogs. It is clear to those skilled in the art when oligonucleotides having natural or non-natural nucleotides may be employed in methods and processes described herein. For example, where processing by an enzyme is called for, usually oligonucleotides consisting solely of natural nucleotides are required. Likewise, where an enzyme has specific oligonucleotide or polynucleotide substrate requirements for activity, e.g., single stranded DNA, RNA/DNA duplex, or the like, then selection of appropriate composition for the oligonucleotide or polynucleotide substrates is well within the knowledge of one of ordinary skill, especially with guidance from treatises, such as Sambrook et al., *Molecular Cloning*, Second Edition (Cold Spring Harbor Laboratory, New York, 1989), and like references. Oligonucleotides and polynucleotides may be single stranded or double stranded.

"Oligonucleotide tag" or "tag" means an oligonucleotide that is attached to a polynucleotide and is used to identify and/or track the polynucleotide in a reaction. Usually, an oligonucleotide tag is attached to the 3'- or 5'-end of a polynucleotide to form a linear conjugate, sometime referred to herein as a "tagged polynucleotide," or equivalently, an "oligonucleotide tag-polynucleotide conjugate," or "tag-polynucleotide conjugate." Oligonucleotide tags may vary widely in size and compositions; the following references provide guidance for selecting sets of oligonucleotide tags appropriate for particular embodiments: Brenner, U.S. Pat. No. 5,635,400; Brenner et al., *Proc. Natl. Acad. Sci.*, 97: 1665; Shoemaker et al. (1996) *Nature Genetics*, 14:450; Morris et al., EP Patent Pub. 0799897A1; Wallace, U.S. Pat. No. 5,981,179; and the like. In different applications of the invention, oligonucleotide tags can each have a length within a range of from 4 to 36 nucleotides, or from 6 to 30 nucleotides, or from 8 to 20 nucleotides, respectively. A tag that is useful in the present invention to identify samples captured from a specific patient or other source is of sufficient length and complexity to distinguish it from sequences that identify other patients or sources of DNA being assayed in parallel. In one aspect, oligonucleotide tags are used in sets, or repertoires, wherein each oligonucleotide tag of the set has a unique nucleotide sequence. In some embodiment, particularly where oligonucleotide tags are used to sort polynucleotides, or where they are identified by specific hybridization, each oligonucleotide tag of such a set has a melting temperature that is substantially the same as that of every other member of the same set. In such aspects, the melting temperatures of oligonucleotide tags within a set are within 10° C. of one another; in another embodiment, they are within 5° C. of one another; and in another embodiment, they are within 2° C. of one another. In another aspect, oligonucleotide tags are members of a minimally cross-hybridizing set. That is, the nucleotide sequence of each member of such a set is sufficiently different from that of every other member of the set that no member can form a stable duplex with the complement of any other member under stringent hybridization conditions. In one aspect, the nucleotide sequence of each member of a minimally cross-hybridizing set differs from those of every other member by at least two nucleotides. Such a set of oligonucleotide tags may have a size in the range of from two, three, four, five etc., up to ten and several tens to many thousands, or even millions, e.g., 50 to $1.6 \times 10^6$. In another embodiment, such a size is in the range of from 200 to 40,000; or from 200 to 40,000; or from 200 to 10,000.

In one embodiment, an amplifiable probe of the invention comprises at least one oligonucleotide tag that is replicated and labeled to produce a labeled oligonucleotide probe. Alternatively, where patient specific tags are envisioned the tag can be detected by stringent hybridization or alternatively sequenced along with the target sequence. In one embodiment, labeled oligonucleotide probes are hybridized to a microarray of tag complements for detection. In this embodiment, for each different locus of each different genome (e.g., from distinct patients, patient samples or other sources) there is a unique labeled oligonucleotide tag. That is, the pair consisting of (i) the nucleotide sequence of the oligonucleotide tag and (ii) a label that generates detectable signal are uniquely associated with a particular locus of a particular genome. The nature of the label on an oligonucleotide tag can be based on a wide variety of physical or chemical properties including, but not limited to, light absorption, fluorescence, chemiluminescence, electrochemiluminescence, mass, charge, and the like. The signals based on such properties can be generated directly or indirectly. For example, a label can be a fluorescent molecule covalently attached to an amplified oligonucleotide tag that directly generates an optical signal. Alternatively, a label can comprise multiple components, such as a hapten-antibody complex, that, in turn, may include fluorescent dyes that generated optical signals, enzymes that generate products that produce optical signals, or the like. Preferably, the label on an oligonucleotide tag is a fluorescent label that is directly or indirectly attached to an amplified oligonucleotide tag. In one aspect, such fluorescent label is a fluorescent dye or quantum dot selected from a group consisting of from 2 to 6 spectrally resolvable fluorescent dyes or quantum dots. In a different embodiment, a set of samples could be queried serially, i.e. using one tag at a time, with each of the tags that represent different patients, samples, etc., wherein each tag is labeled with the same label, and what is detected is binding or no binding to members of the set of samples, thereby identifying in each round a given patient's sample.

Fluorescent labels and their attachment to oligonucleotides, such as oligonucleotide tags, are described in many reviews, including Haugland, *Handbook of Fluorescent Probes and Research Chemicals*, Ninth Edition (Molecular Probes, Inc., Eugene, 2002); Keller and Manak, DNA Probes, 2nd Edition (Stockton Press, New York, 1993); Eckstein, editor, *Oligonucleotides and Analogues: A Practical Approach* (IRL Press, Oxford, 1991); Wetmur, *Critical Reviews in Biochemistry and Molecular Biology*, 26:227-259 (1991); and the like. Particular methodologies applicable to the invention are disclosed in the following sample of references: Fung et al., U.S. Pat. No. 4,757,141; Hobbs, Jr., et al. U.S. Pat. No. 5,151,507; Cruickshank, U.S. Pat. No. 5,091,519. In one aspect, one or more fluorescent dyes are used as labels for labeled target sequences, e.g., as disclosed by Menchen et al., U.S. Pat. No. 5,188,934 (4,7-dichlorofluorscein dyes); Begot et al., U.S. Pat. No. 5,366,860 (spectrally resolvable rhodamine dyes); Lee et al., U.S. Pat. No. 5,847,162 (4,7-dichlororhodamine dyes); Khanna et al., U.S. Pat. No. 4,318,846 (ether-substituted fluorescein dyes); Lee et al., U.S. Pat. No. 5,800,996 (energy transfer dyes); Lee et al., U.S. Pat. No. 5,066,580 (xanthine dyes): Mathies et al., U.S. Pat. No. 5,688,648 (energy transfer dyes); and the like. Labelling can also be carried out with quantum dots, as disclosed in the following patents and patent publications: U.S. Pat. Nos. 6,322,901; 6,576,291; 6,423,551; 6,251,303; 6,319,426; 6,426,513; 6,444,143; 5,990,479; 6,207,392; 2002/0045045; 2003/0017264; and the like. As used herein, the term "fluorescent label" includes a signaling moiety that conveys information through the fluorescent absorption and/or emission properties of one or more molecules. Such fluorescent properties include fluorescence intensity, fluorescence life time, emission spectrum characteristics, energy transfer, and the like.

Commercially available fluorescent nucleotide analogues readily incorporated into the labeling oligonucleotides include, for example, Cy3-dCTP, Cy3-dUTP, Cy5-dCTP, Cy5-dUTP (Amersham Biosciences, Piscataway, N.J.), fluorescein-12-dUTP, tetramethylrhodamine-6-dUTP, TEXAS RED™-5-dUTP, CASCADE BLUE™-7-dUTP, BODIPY TMFL-14-dUTP, BODIPY TMR-14-dUTP, BODIPY TMTR-14-dUTP, RHODAMINE GREEN™-5-dUTP, OREGON GREENR™ 488-5-dUTP, TEXAS RED™-12-dUTP, BODIPY TM 630/650-14-dUTP, BODIPY TM 650/665-14-dUTP, ALEXA FLUOR™ 488-5-dUTP, ALEXA FLUOR™ 532-5-dUTP, ALEXA FLUOR™ 568-5-dUTP, ALEXA FLUOR™ 594-5-dUTP, ALEXA FLUOR™ 546-14-dUTP, fluorescein-12-UTP, tetramethylrhodamine-6-UTP, TEXAS RED™-5-UTP, mCherry, CASCADE BLUE™-7-UTP, BODIPY TM FL-14-UTP, BODIPY TMR-14-UTP, BODIPY TM TR-14-UTP, RHODAMINE GREEN™-5-UTP, ALEXA FLUOR™ 488-5-UTP, LEXA FLUOR™ 546-14-UTP (Molecular Probes, Inc. Eugene, Oreg.). Protocols are available for custom synthesis of nucleotides having other fluorophores. Henegariu et al., "Custom Fluorescent-Nucleotide Synthesis as an Alternative Method for Nucleic Acid Labeling," *Nature Biotechnol.* 18:345-348 (2000).

Other fluorophores available for post-synthetic attachment include, inter alia, ALEXA FLUOR™ 350, ALEXA FLUOR™ 532, ALEXA FLUOR™ 546, ALEXA FLUOR™ 568, ALEXA FLUOR™ 594, ALEXA FLUOR™ 647, BODIPY 493/503, BODIPY FL, BODIPY R6G, BODIPY 530/550, BODIPY TMR, BODIPY 558/568, BODIPY 558/568, BODIPY 564/570, BODIPY 576/589, BODIPY 581/591, BODIPY 630/650, BODIPY 650/665, Cascade Blue, Cascade Yellow, Dansyl, lissamine rhodamine B, Marina Blue, Oregon Green 488, Oregon Green 514, Pacific Blue, rhodamine 6G, rhodamine green, rhodamine red, tetramethyl rhodamine, Texas Red (available from Molecular Probes, Inc., Eugene, Oreg.), and Cy2, Cy3.5, Cy5.5, and Cy7 (Amersham Biosciences, Piscataway, N.J. USA, and others).

FRET tandem fluorophores may also be used, such as PerCP-Cy5.5, PE-Cy5, PE-Cy5.5, PE-Cy7, PE-Texas Red, and APC-Cy7; also, PE-Alexa dyes (610, 647, 680) and APC-Alexa dyes.

Metallic silver particles may be coated onto the surface of the array to enhance signal from fluorescently labeled oligos bound to the array. Lakowicz et al. (2003) *BioTechniques* 34:62.

Biotin, or a derivative thereof, may also be used as a label on a detection oligonucleotide, and subsequently bound by a detectably labeled avidin/streptavidin derivative (e.g. phycoerythrin-conjugated streptavidin), or a detectably labeled anti-biotin antibody. Digoxigenin may be incorporated as a label and subsequently bound by a detectably labeled anti-digoxigenin antibody (e.g. fluoresceinated anti-digoxigenin). An aminoallyl-dUTP residue may be incorporated into a detection oligonucleotide and subsequently coupled to an N-hydroxy succinimide (NHS) derivatized fluorescent dye, such as those listed supra. In general, any member of a conjugate pair may be incorporated into a detection oligonucleotide provided that a detectably labeled conjugate partner can be bound to permit detection. As used herein, the term antibody refers to an antibody molecule of any class, or any sub-fragment thereof, such as an Fab.

Other suitable labels for detection oligonucleotides may include fluorescein (FAM), digoxigenin, dinitrophenol (DNP), dansyl, biotin, bromodeoxyuridine (BrdU), hexahistidine (6×His), phosphor-amino acids (e.g. P-tyr, P-ser, P-thr), or any other suitable label. In one embodiment the following hapten/antibody pairs are used for detection, in which each of the antibodies is derivatized with a detectable label: biotin/α-biotin, digoxigenin/a-digoxigenin, dinitrophenol (DNP)/α-DNP, 5-Carboxyfluorescein (FAM)/α-FAM.

As mentioned above, oligonucleotide tags can be indirectly labeled, especially with a hapten that is then bound by a capture agent, e.g., as disclosed in Holtke et al., U.S. Pat. Nos. 5,344,757; 5,702,888; and 5,354,657; Huber et al., U.S. Pat. No. 5,198,537; Miyoshi, U.S. Pat. No. 4,849,336; Misiura and Gait, PCT publication WO 91/17160; and the like. Many different hapten-capture agent pairs are available for use with the invention, either with a target sequence or with a detection oligonucleotide used with a target sequence, as described below. Exemplary, haptens include, biotin, des-biotin and other derivatives, dinitrophenol, dansyl, fluorescein, CY5, and other dyes, digoxigenin, and the like. For biotin, a capture agent may be avidin, streptavidin, or antibodies. Antibodies may be used as capture agents for the other haptens (many dye-antibody pairs being commercially available, e.g., Molecular Probes, Eugene, Oreg.).

"Polymerase chain reaction," or "PCR," means a reaction for the in vitro amplification of specific DNA sequences by the simultaneous primer extension of complementary strands of DNA. In other words, PCR is a reaction for making multiple copies or replicates of a target nucleic acid flanked by primer binding sites, such reaction comprising one or more repetitions of the following steps: (i) denaturing the target nucleic acid, (ii) annealing primers to the primer binding sites, and (iii) extending the primers by a nucleic acid polymerase in the presence of nucleoside triphosphates. Usually, the reaction is cycled through different temperatures optimized for each step in a thermal cycler instrument. Particular temperatures, durations at each step, and rates of change between steps depend on many factors well-known to those of ordinary skill in the art, e.g., exemplified by the references: McPherson et al., editors, *PCR: A Practical Approach* and *PCR2: A Practical Approach* (IRL Press, Oxford, 1991 and 1995, respectively). For example, in a conventional PCR using Taq DNA polymerase, a double stranded target nucleic acid may be denatured at a temperature greater than 90° C., primers annealed at a temperature in the range 50-75° C., and primers extended at a temperature in the range 72-78° C.

The term "PCR" encompasses derivative forms of the reaction, including but not limited to, RT-PCR, real-time PCR, nested PCR, quantitative PCR, multiplexed PCR, and the like. Reaction volumes range from a few hundred nanoliters, e.g., 200 mL, to a few hundred microliters, e.g., 200 microliters. "Reverse transcription PCR," or "RT-PCR," means a PCR that is preceded by a reverse transcription reaction that converts a target RNA to a complementary single stranded DNA, which is then amplified, e.g., Tecott et al., U.S. Pat. No. 5,168,038. "Real-time PCR" means a PCR for which the amount of reaction product, i.e., amplicon, is monitored as the reaction proceeds. There are many forms of real-time PCR that differ mainly in the detection chemistries used for monitoring the reaction product, e.g., Gelfand et al., U.S. Pat. No. 5,210,015 ("Taqman"); Wittwer et al., U.S. Pat. Nos. 6,174,670 and 6,569,627 (intercalating dyes); Tyagi et al., U.S. Pat. No. 5,925,517 (molecular beacons). Detection chemistries for real-time PCR are reviewed in Mackay et al., *Nucleic Acids Research*, 30:1292-1305 (2002). "Nested PCR" means a two-stage PCR wherein the amplicon of a first PCR becomes the sample for a second PCR using a new set of primers, at least one of which binds to an interior location of the first amplicon. As used herein, "initial primers" in reference to a nested amplification reaction mean the primers used to generate a first amplicon, and "secondary primers" mean the one or more primers used to generate a second, or nested, amplicon. "Multiplexed PCR" means a PCR wherein multiple target sequences (or a single target sequence and one or more reference sequences) are simultaneously carried out in the same reaction mixture, e.g. Bernard et al. (1999) *Anal. Biochem.*, 273:221-228 (two-color real-time PCR). Usually, distinct sets of primers are employed for each sequence being amplified. "Quantitative PCR" means a PCR designed to measure the abundance of one or more specific target sequences in a sample or specimen. Quantitative PCR includes both absolute quantitation and relative quantitation of such target sequences. Quantitative measurements are made using one or more reference sequences that may be assayed separately or together with a target sequence. The reference sequence may be endogenous or exogenous to a sample or specimen, and in the latter case, may comprise one or more competitor templates. Typical endogenous reference sequences include segments of transcripts of the following genes: β-actin, GAPDH, $β_2$-microglobulin, ribosomal RNA, and the like. Techniques for quantitative PCR are well-known to those of ordinary skill in the art, as exemplified in the following references: Freeman et al., *Biotechniques*, 26:112-126 (1999); Becker-Andre et al., *Nucleic Acids Research*, 17:9437-9447 (1989); Zimmerman et al., *Biotechniques*, 21:268-279 (1996); Diviacco et al., *Gene*, 122:3013-3020 (1992); Becker-Andre et al., *Nucleic Acids Research*, 17:9437-9446 (1989); and the like.

"Polymorphism" or "genetic variant" means a substitution, inversion, insertion, or deletion of one or more nucleotides at a genetic locus, or a translocation of DNA from one genetic locus to another genetic locus. In one aspect, polymorphism means one of multiple alternative nucleotide sequences that may be present at a genetic locus of an individual and that may comprise a nucleotide substitution, insertion, or deletion with respect to other sequences at the same locus in the same individual, or other individuals within a population. An individual may be homozygous or heterozygous at a genetic locus; that is, an individual may have the same nucleotide sequence in both alleles, or have a different nucleotide sequence in each allele, respectively. In one aspect, insertions or deletions at a genetic locus comprises the addition or the absence of from 1 to 10 nucleotides at such locus, in comparison with the same locus in another individual of a population (or another allele in the same individual). Usually, insertions or deletions are with respect to a major allele at a locus within a population, e.g., an allele present in a population at a frequency of fifty percent or greater.

"Primer" includes an oligonucleotide, either natural or synthetic, that is capable, upon forming a duplex with a polynucleotide template, of acting as a point of initiation of nucleic acid synthesis and being extended from its 3' end along the template so that an extended duplex is formed. The sequence of nucleotides added during the extension process are determined by the sequence of the template polynucleotide. Usually primers are extended by a DNA polymerase. Primers usually have a length in the range of between 3 to 36 nucleotides, also 5 to 24 nucleotides, also from 14 to 36 nucleotides. Primers within the scope of the invention can be universal primers or non-universal primers. Pairs of primers can flank a sequence of interest or a set of sequences of interest. Primers and probes can be degenerate in sequence. Primers within the scope of the present invention bind adjacent to the target sequence, whether it is the sequence to be captured for analysis, or a tag that it to be copied.

"Solid support," "support," and "solid phase support" are used interchangeably and refer to a material or group of materials having a rigid or semi-rigid surface or surfaces. In many embodiments, at least one surface of the solid support will be substantially flat, although in some embodiments it may be desirable to physically separate synthesis regions for different compounds with, for example, wells, raised regions, pins, etched trenches, or the like. According to other embodiments, the solid support(s) will take the form of beads, resins, gels, microspheres, or other geometric configurations. Microarrays usually comprise at least one planar solid phase support, such as a glass microscope slide. Semisolid supports and gel supports are also useful in the present invention, especially when polony amplification is used.

"Specific" or "specificity" in reference to the binding of one molecule to another molecule, such as a target sequence to a probe, means the recognition, contact, and formation of a stable complex between the two molecules, together with substantially less recognition, contact, or complex formation of that molecule with other molecules. In one aspect, "specific" in reference to the binding of a first molecule to a second molecule means that to the extent the first molecule recognizes and forms a complex with another molecules in a reaction or sample, it forms the largest number of the complexes with the second molecule. Preferably, this largest number is at least fifty percent. Generally, molecules involved in a specific binding event have areas on their surfaces or in cavities giving rise to specific recognition between the molecules binding to each other. Examples of specific binding include antibody-antigen interactions, enzyme-substrate interactions, formation of duplexes or triplexes among polynucleotides and/or oligonucleotides, receptor-ligand interactions, and the like. As used herein, "contact" in reference to specificity or specific binding means two molecules are close enough that weak non-covalent chemical interactions, such as van der Waal forces, hydrogen bonding, base-stacking interactions, ionic and hydrophobic interactions, and the like, dominate the interaction of the molecules.

"Spectrally resolvable" in reference to a plurality of fluorescent labels means that the fluorescent emission bands of the labels are sufficiently distinct, i.e., sufficiently non-overlapping, that molecular tags to which the respective labels are attached can be distinguished on the basis of the fluorescent signal generated by the respective labels by standard photodetection systems, e.g., employing a system of band pass filters and photomultiplier tubes, or the like, as exemplified by the systems described in U.S. Pat. Nos. 4,230,558; 4,811,218, or the like, or in Wheeless et al., pgs. 21-76, in *Flow Cytometry: Instrumentation and Data Analysis* (Academic Press, New York, 1985). In one aspect, spectrally resolvable organic dyes, such as fluorescein, rhodamine, and the like, means that wavelength emission maxima are spaced at least 20 nm apart, and in another aspect, at least 40 nm apart. In another aspect, chelated lanthanide compounds, quantum dots, and the like, spectrally resolvable means that wavelength emission maxima are spaced at least 10 nm apart, and in a further aspect, at least 15 nm apart.

"$T_m$" is used in reference to "melting temperature." Melting temperature is the temperature at which a population of double-stranded nucleic acid molecules becomes half dissociated into single strands. Several equations for calculating the $T_m$ of nucleic acids are well known in the art. As indicated by standard references, a simple estimate of the $T_m$ value may be calculated by the equation. $T_m=81.5+0.41$ (% G+C), when a nucleic acid is in aqueous solution at 1 M NaCl (see e.g., Anderson and Young, "Quantitative Filter Hybridization," in *Nucleic Acid Hybridization* (1985). Other references (e.g., Allawi, H. T. & Santa Lucia, J., Jr., *Biochemistry* 36, 10581-94 (1997)) include alternative methods of computation which take structural and environmental, as well as sequence characteristics into account for the calculation of $T_m$.

"Sample" means a quantity of material from a biological, environmental, medical, or patient source in which detection or measurement of target nucleic acids is sought. On the one hand it is meant to include a specimen or culture (e.g., microbiological cultures). On the other hand, it is meant to include both biological and environmental samples. A sample may include a specimen of synthetic origin. Biological samples may be animal, including human, fluid, solid (e.g., stool or tissue), as well as liquid and solid food and feed products and ingredients such as dairy items, vegetables, meat and meat by-products, and waste. Biological samples may include materials taken from a patient including, but not limited to cultures, cells, tissues, blood, saliva, cerebral spinal fluid, pleural fluid, milk, lymph, sputum, semen, needle aspirates, and the like. Biological samples may be obtained from all of the various families of domestic animals, as well as feral or wild animals, including, but not limited to, such animals as ungulates, bear, fish, rodents, etc. Environmental samples include environmental material such as surface matter, soil, water and industrial samples, as well as samples obtained from food and dairy processing instruments, apparatus, equipment, utensils, disposable and non-disposable items. These examples are not to be construed as limiting the sample types applicable to the present invention.

It is to be understood that the embodiments of the present invention which have been described are merely illustrative of some of the applications of the principles of the present invention. Numerous modifications may be made by those skilled in the art based upon the teachings presented herein without departing from the true spirit and scope of the invention. The contents of all references, patents and published patent applications cited throughout this application are hereby incorporated by reference in their entirety for all purposes.

The following examples are set forth as being representative of the present invention. These examples are not to be construed as limiting the scope of the invention as these and other equivalent embodiments will be apparent in view of the present disclosure, figures, tables, and accompanying claims.

EXAMPLE I

Two-Dimensional Genotyping

Figure 3:
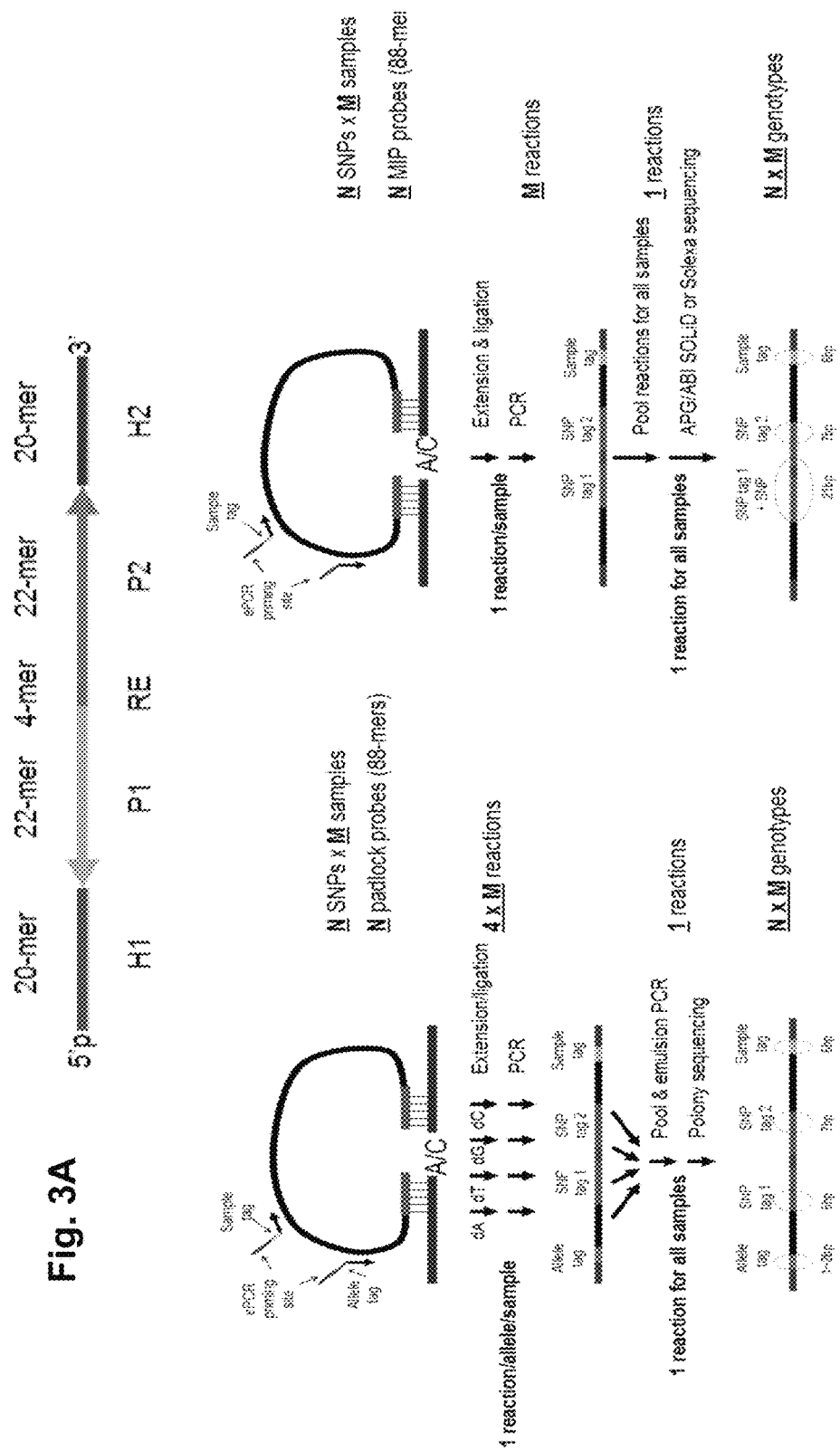
FIGS. 3A-3C schematically depict a two-dimensional genotyping by polony sequencing on padlock probes assay. (A) depicts the design of padlock probes. Similar to molecular inversion probes (MIPs), each padlock probe has two locus-specific capturing sequences (H1 and H2) at the 3'- and 5'-ends. All probes share two common priming sites (P1 and P2) and a restriction endonuclease recognition site in the middle. (B) depicts polony sequencing on padlock probes. Padlock probes for N SNPs are annealed to genomic DNA and circularized similar to MIPs. This part of procedure is carried out one reaction for each allele and each sample separately. After circularization and release of padlocks, PCR is performed with primers carrying allele tags and sample tags. As a result, the amplicons for M samples are tagged with unique barcodes and pooled for polony sequencing. SNPs are identified based on the 6+7 base pairs within the capturing sequences H1 and H2, which can accommodate up to 67 million ($4^{13}$) loci. For a small faction of SNPs with the same 13 base pair barcodes, additional barcodes can be added between H1 and P1 or P2 and H2. (C) depicts an alternative strategy based on sequencing methods with longer read length. For sequencing methods with sufficiently long read lengths, padlock probes are used to capture the SNPs themselves for sequencing. Since no allele-specific extension is involved, the circularization can be carried out in one tube instead of four, thereby increasing throughput.

A large number of padlock probes (oligonucleotide probes that can circularize) can be used to specifically capture single nucleotide polymorphisms (SNPs) from genomic DNA, and the associated SNP identities and genotypes can be subsequently assessed by massively parallel DNA sequencing (FIG. 3). Without intending to be bound by theory, padlock probes likely provide the highest specificity among current genotyping methods because the circularization involves the combination of (i) co-operative annealing of two short sequences to a target in a uni-molecular fashion, (ii) allelic-specific single-base extension, (iii) allelic-specific ligation. In contrast, both Affymetrix's GENECHIP® and Illumina's INFINIUM™ assay involve a hybridization step that has an inherent limitation in distinguishing very similar sequences. Without intending to be bound by theory, padlock probes likely represent the best opportunity to further increase the number of SNPs determined in one assay from approximately 500,000 to approximately 10 million. Furthermore, combining padlock probes with DNA sequencing creates a distinct feature not possible with any of the current array-based methods: multiplexing on a large number of samples (Syvanen (2005) *Nat. Genet.* 37:S5-10). To achieve two dimensional (2D) genotyping, padlock probes circularized on different samples will be tagged with unique sample barcodes and pooled for DNA sequencing. The genotype at a given SNP locus of a certain sample will then be decoded by the combinations of three barcodes, allele barcode, locus barcode and sample barcode, all obtained in a single sequencing run. This provides an enormous advantage over existing technologies in that a single technology platform can be used for projects with a wide spectrum of SNP number and sample size combinations.

Development of 2D genotyping relies on recent advances large-scale DNA synthesis. Making millions of padlock probes is non-trivial given the current capability of solid-phase DNA synthesis. Padlock probes are approximately 100 base pairs in length and, thus, genotyping one million SNPs requires the synthesis of roughly approximately 100 megabases of DNA in a large quantity. Such large scale synthesis would be prohibitively expensive under conventional DNA synthesis methods. With column-based solid phase DNA synthesis, the cost is approximately $0.05/base, which translates to a total cost of approximately $5,000,000 for probe synthesis alone. Moreover, oligonucleotides longer than 70 base pairs generally require additional polyacrylamide gel electrophoresis (PAGE) purifications because of the presence of a high percentage of truncated sequences. Thus, it is impractical to produce millions of padlock probes using conventional DNA synthesis methods.

Figure 4:
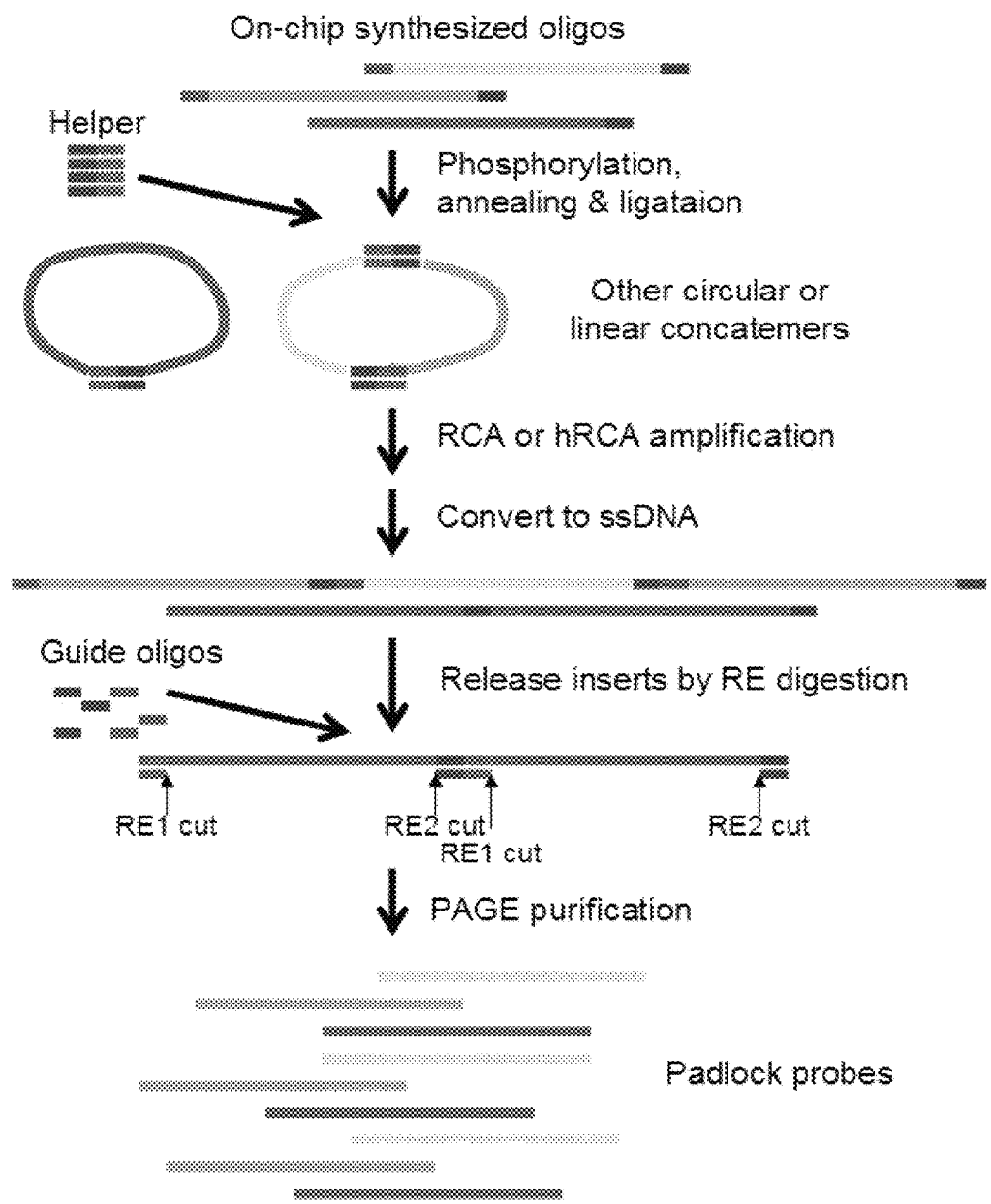
FIG. 4 schematically depicts the large-scale production of padlock probes from oligonucleotides synthesized on programmable DNA chips. On-chip synthesized oligonucleotides have common 3' and 5'-adaptors flanking the padlock probes. The adaptors and a circularization "helper" oligo have reverse complementary sequences so that linear oligonucleotide can be circularized and amplified. The adaptors also have a Type IIs restriction recognition site, so that padlock probes can be released by oligo-guided restriction endonuclease digestion on single-stranded concatemers.

The present invention is based in part on the use of DNA programmable chips (Tian et al. (2004) Nature 432:1050) to make padlock probes. More specifically, a large number of oligonucleotides will be synthesized on DNA programmable chips in small quantity (approximately femtomole scale). These oligonucleotides will then be amplified as a pool to a large quantity using in vitro polymerase cloning methods (Dahl et al. (2004) *Proc. Natl. Acad. Sci. U.S.A.* 101:4548; Hutchinson et al. (2005) *Proc. Natl. Acad. Sci. U.S.A.* 102:17332; Zhang et al. (2006) *Nat. Biotechnol.* 24:680), and finally converted to single-stranded padlock probes through a series of enzymatic treatments (FIG. 4). This procedure will facilitate the synthesis of millions of padlock probes at a very low cost.

Figure 5A:
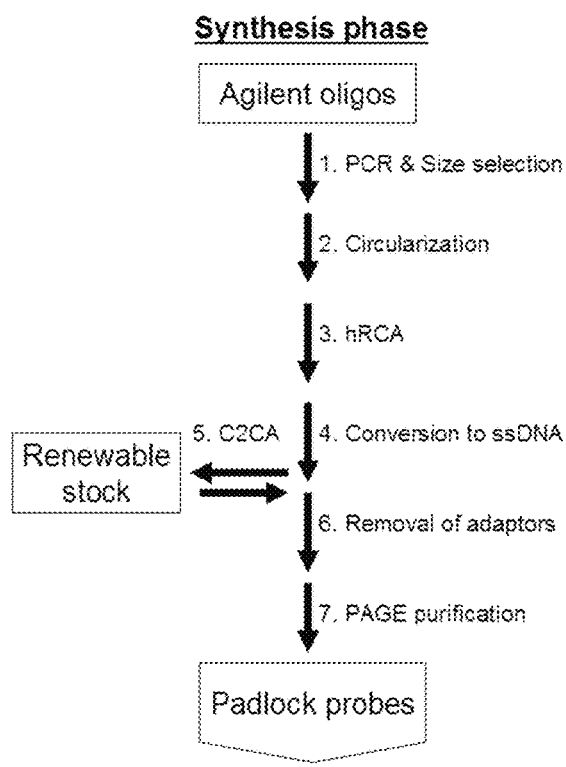
FIGS. 5A-5B depict an overview of the technology development. (A) shows the twelve steps of technology development. (B) shows the design of chip-synthesized oligonucleotides.
Figure 5B:
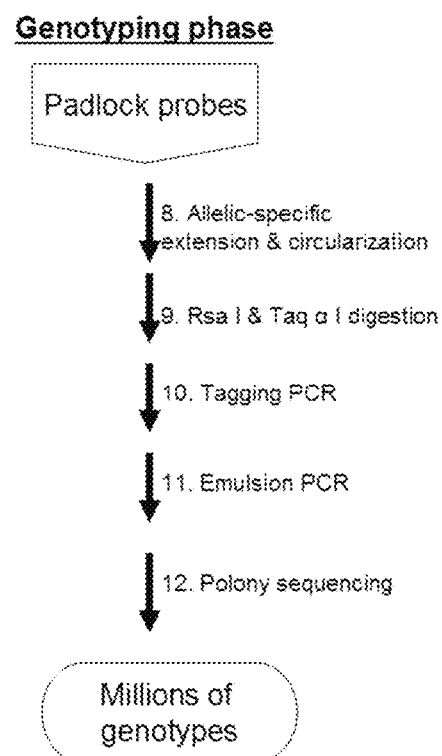

2D genotyping can be divided into two phases: the synthesis phase and the genotyping/sequencing phase (FIG. 5). Protocol development of the synthesis phase using long oligonucleotides synthesized by the conventional column-based method at Integrated DNA Technology (IDT, IA), and ~30,000 oligonucleotides synthesized on Agilent prototype chips was recently completed. Protocols for the first three steps in the genotyping phase have also been developed. Some important results will be presented in detail in the examples set forth below.

EXAMPLE II

Circularization and Amplification of Long Oligonucleotides Synthesized on DNA Programmable Chips (Steps 1-5)

Performing genotyping of one million SNPs on one sample requires approximately 150 ng of padlock probes that contain one million species of a total length of 88 Mbp (assuming 400 ng of genomic template and a probe:target ratio of 6:1). With the most recent chip-synthesis technology at Agilent, one programmable chip can produce 22,000 or 44,000 long oligonucleotides at the scale of approximately 1 femtomole per oligonucleotide. In order to achieve the goal of ultra-low-cost SNP genotyping, a large quantity of padlock probes must be regenerated from oligonucleotides synthesized on a single set of Agilent chips at a low cost (less than $10/150 ng). Rolling circle amplification/hyperbranched rolling circle amplification (RCA/hRCA) on circularized oligonucleotides will be performed for this purpose.

RCA/hRCA has at least three major advantages over PCR-based methods. First, the yield of RCA/hRCA is usually approximately 10- to 100-fold higher than PCR. Second, RCA/hRCA has a much lower bias compared with PCR. Finally, and most importantly, because of the isothermal nature of RCA/hRCA, non-specific false priming of amplification primers is not an issue. In contrast, truncated or chimeric amplicons have often been observed with PCR amplified oligonucleotides in our laboratory, because, when amplifying a complex pool of $10^{4-6}$ partially homologous sequences, amplicons often compete with primers in priming during the late stages of thermal cycling.

Figure 6A:
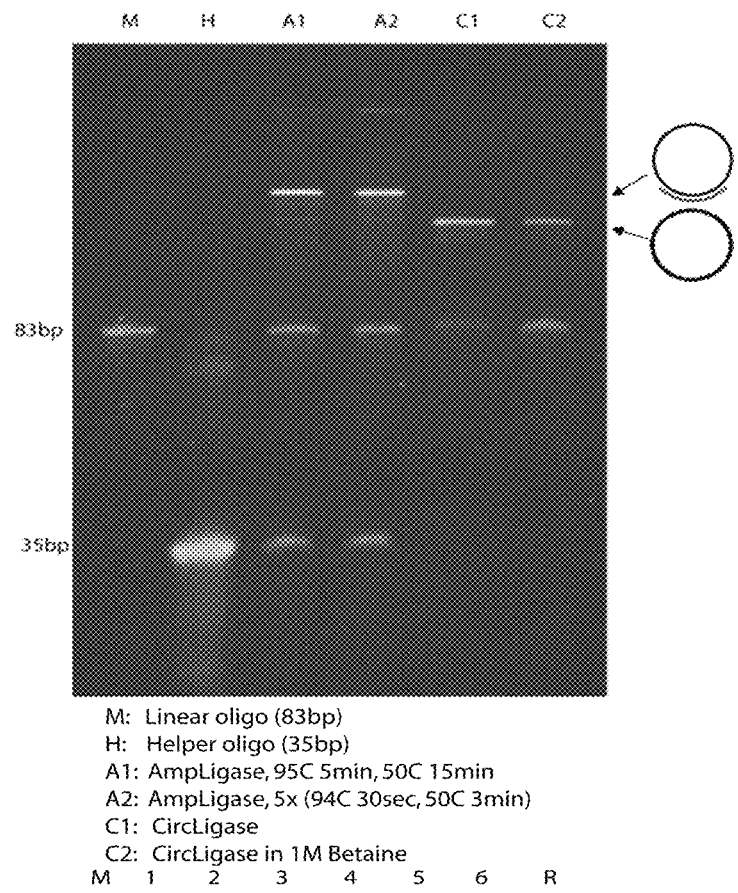
FIGS. 6A-6B depict gels showing circularization of oligonucleotides. (A) is a comparison of helper oligo dependent and independent circularization using AmpLigase or CircLigase. The products are run on a non-denaturing polyacrylamide gel. The 83 base pair oligo is 500 nM and the 35 base pair helper oligo is 300 nM. (C) is a comparison of circularization efficiency using AmpLigase or T4 DNA Ligase at different oligo:helper ratios. The linear form is barely visible in all the six circularization reactions, indicating a near complete circularization efficiency.

Several options to convert linear oligonucleotides synthesized from programmable DNA chips into the circular form were investigated. One way that this circularization of linear oligonucleotides can be performed is through the use of the DNA ligase, CircLigase, which catalyzes intra-molecular ligation of single-stranded DNA. One major advantage of using CircLigase is that it does not require long flanking sequences which is especially desirable since with our current synthesis method the quality and yield decreases as the length of oligonucleotide goes up. However, one major issue associated with CircLigase is that its efficiency depends on DNA sequence composition, and hence using this enzyme could lead to a biased library. Hypothesizing that the efficiency could depend on the GC content of oligonucleotides, the circularization reaction was tested in the presence of betaine, which cancels out the difference between A:T and G:C base pairing. It was determined that CircLigase had ligation activity in the presence of 1 M betaine, although the circularization efficiency was slightly lower than that without betaine (FIG. 6A). Further characterization of the ligation bias of CircLigase and the effect of betaine will be performed using polony sequencing of the circularized library.

Figure 6B:
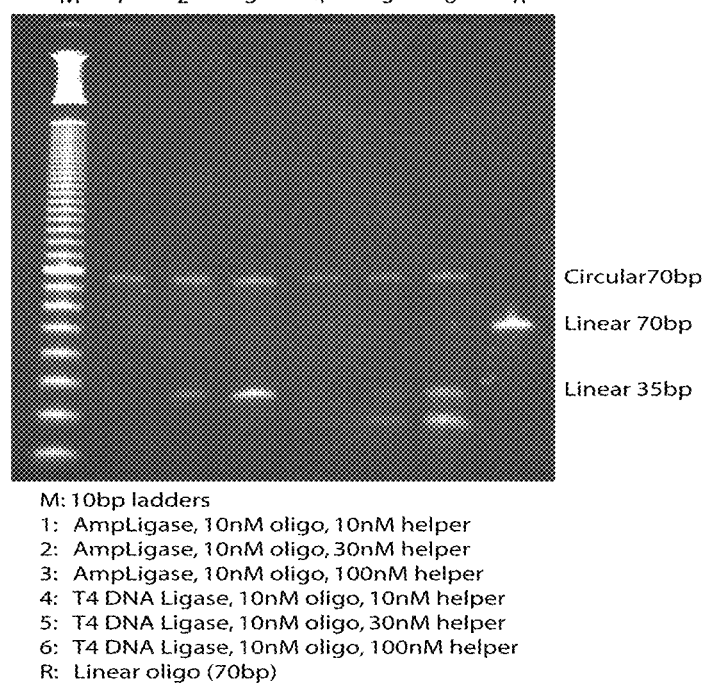
Figure 7D:
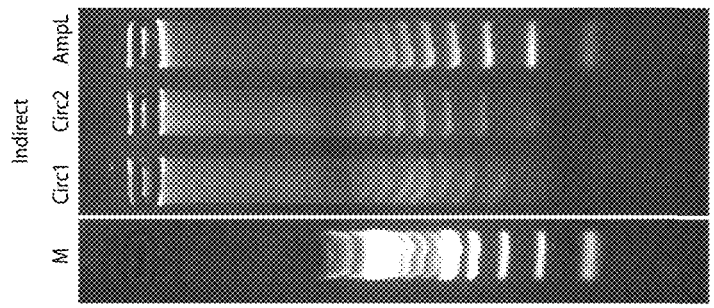
FIGS. 7A-7D depict the hyper-branched rolling circle amplification (hRCA) of oligonucleotides. (A) shows two circularization methods. In the direct circularization protocol, oligonucleotides are phosphorylated at 5' ends using polynucleotide kinase (PNK), then circularized. In the indirect protocol, linear amplification is first performed to obtain the reverse complementary strands with 5' phosphate group. The reverse strands are then circularized. The helper oligos are different in the two protocols, so the size of circles in the direct method is 3 base pairs larger. (B) shows circularization of a degenerate 70-mer (synthesized at IDT) with the direct and indirect method, and amplification with hRCA using Bst polymerase. The amplicons were analyzed by electrophoresis on a 6% denaturing polyacrylamide gel. (C, D) show circularization of 22,000 137-mers synthesized on an Agilent chip using the direct and indirect method, and subsequently amplified with two rounds of hRCA (phi29 polymerase in the first round and Bst polymerase in the second round). The amplicons were resolved on non-denaturing 1.5% agarose gels. M: 100 base pair ladder; Circ1: Circularized with CircLigase; Circ2: circularized with CircLigase and 1 M betaine; AmpL: circularized with AmpLigase with a helper oligo.
Figure 7C:
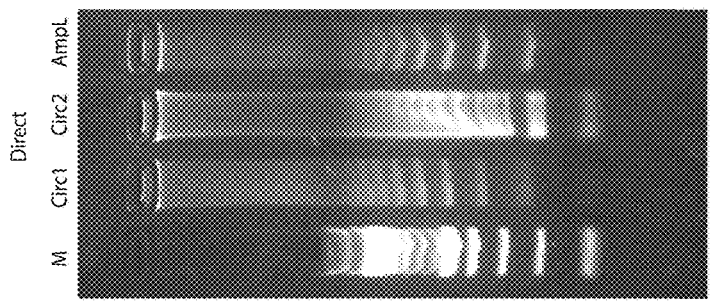
Figure 7B:
Figure 7A:
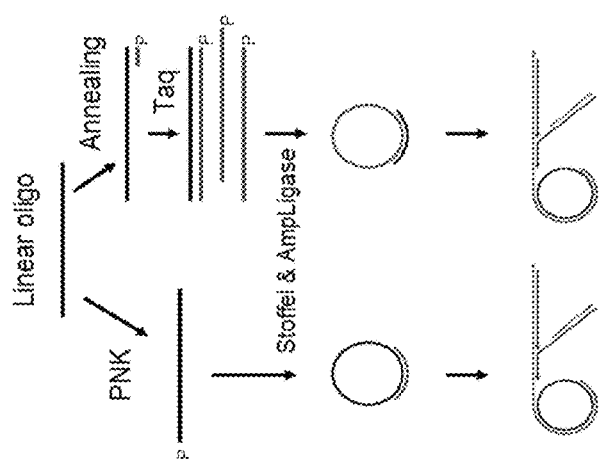

A second circularization method involves the use of a "helper" oligonucleotide and a double-stranded DNA ligase, such as T4 DNA ligase, Taq DNA ligase or AmpLigase. This method relies upon the same circularization principal involved in the closure of padlock probes. Without intending to be bound by theory, this circularization method has several advantages. First, the use of a reasonably long helper oligonucleotide along with a thermostable ligase will ensure highly specific ligation. Second, this approach will allow significant flexibility as through the use of different helper oligos, different pools of chip-synthesized oligos could be selectively circularized. Lastly, the helper oligo method will allow the selective circularization of properly sized oligos as only oligonucleotides with intact adaptors on both ends will be circularized. Near-complete ligation was obtained with either T4 DNA ligase or AmpLigase at different oligo/helper ratios (FIG. 6B).

After the downstream protocols for probe production were established, and the padlock probes were tested for genotyping, unexpected issues arose associated with the circularization protocol. A significant reduction of probe complexity was observed using the indirect circularization protocol, indicating the circularization was either extremely inefficient or biased towards certain probe sequences. With the direct circularization method, a wide distribution of size of padlock probes was observed after removing adaptors. Only a very small percentage of probes had the expected size. In contrast, the protocol worked well with the reference oligonucleotides synthesized at IDT, indicating (without being limited by theory) that the oligonucleotides synthesized on Agilent's chips could be a mixed population of good ones and bad (e.g., truncated and/or branched) ones. Accordingly, a pre-circularization PCR amplification and size selection step (Step 1) was included to select for full length oligonucleotides. T7 exonuclease was also used to convert double-stranded amplicons to single-stranded sequences prior to circularization, which turned out to be critical in improving circularization efficiency.

Protocols for direct and indirect circularization of oligonucleotides have been established (FIG. 6). Good results have been obtained using three different amplification methods (RCA, hRCA and C2CA) (FIG. 7).

One key step in probe production is to produce a large quantity of single-stranded DNA. When the circularized oligonucleotides are amplified via hRCA, the amplicons are double-stranded DNA in a hyperbranched structure. Such amplicons need to be converted to single-stranded DNA before single-stranded padlock probes can be released by oligo-guided restriction endonuclease digestion. The following five protocols to make single-stranded DNA were evaluated in terms of simplicity, efficiency, product purity and cost:

1. hRCA with a phosphorylated reverse primer, followed by lambda exonuclease digestion to remove the reverse strand.
2. hRCA with phorphorothioate protected forward primer, followed by T7 exonuclease digestion to remove the reverse strand.
3. hRCA with a double-biotin modified reverse primer, capture the reverse strands with magnetic bead, on-bead synthesis of the forward strands with the following DNA polymerases, followed by elution of the forward strands with an alkaline denaturation solution.
   i. Bst, Vent exo- (both have strand displacement activity)
   ii. Different variants of Taq (3' exo)
   iii. Klenow exo-, AmpliTaq Stoffel fragment
4. hRCA with an Acrydite modified reverse primer, immobilize the reverse strands with polyacrylamide gel, in-gel synthesis of the forward strands with the aforementioned DNA polymerases, followed by elution of the forward strands with an alkaline denaturation solution.
5. hRCA with d[AUGC]TP, one round of synthesis using the forward primer in the presence of d[ATGC]TP, and USER enzyme digestion. The NEB USER enzyme is a mixture of Uracil DNA glycosylase and Endonuclease VIII that cleaves DNA at uracil. Because dUTP is used in place of dTTP in the hRCA, all amplified molecules will be degraded into small fragments. Only the forward strands synthesized at the 2nd round replication will survive the USER digestion.

All five methods were successfully used to make single-stranded DNA. The first method using lambda exonuclease appeared to be easier and more efficient than the others, and became the method used.

To reduce the cost of probe production, it is critical to construct a renewable pool of padlock probes containing millions of species from one set of programmable DNA chips. This protocol will be based on the combination of Circle-To-Circle Amplification (C2CA) and hRCA (Lizardi et al. (1998) *Nat. Genet.* 19:225; Dahl et al., supra). With C2CA, circular DNA molecules containing a unique restriction endonuclease recognition site are amplified by RCA to form long linear concatemers, which can be digested by the restriction endonuclease with a guide oligo. The resulting monomers are then ligated, so that each circular template molecule is converted into approximately 1000 circles of the reverse complementary strand. This procedure can be repeated multiple times alternating between the "+" strand and the "−" strand to achieve a very high amplification magnitude. C2CA has been shown to have less amplification bias than PCR (Dahl et al., supra), making it an ideal choice for the renewable protocol. The C2CA method was tested on a reference IDT degenerate oligonucleotide as well as 22,000 Agilent oligonucleotides, but a high amplification magnitude as reported by Dahl et al. was not achieved. Without intending to be bound by theory, one likely explanation for these results was that incomplete restriction endonuclease digestion combined with the ligation of a large number of different DNA molecules likely lead to the low amplification. This explanation is consistent with the fact that C2CA was developed for the amplification of a very small number of molecules, not for large-scale preparative purposes. Nevertheless, while the C2CA protocol will be further optimized for preparative purposes, C2CA will also be used for generating a renewable library and hRCA will be used for the generation of a large amount of this library.

EXAMPLE III

Preparation of Padlock Probes from Amplified Oligonucleotides by Oligo-Guided Restriction Endonuclease Digestion (Step 6)

After amplification with RCA/hRCA, padlock probes are present as linear concatemers. Each padlock probe is flanked by adaptors at the 3'- and 5'-ends. RCA amplicons are single-stranded while hRCA amplicons can be converted into single-stranded forms using several methods mentioned above. Oligo-guided restriction endonuclease digestion (Szybalski (1985) *Gene* 40:169; Kim et al. (1988) *Science* 240:504; Zhu (1989) *Anal. Biochem.* 177:120; Podhajska et al. (1992) *Meth. Enzymol.* 216:303) is used to release the "inserts" from linear concatemers (FIG. 4). Because each padlock probe has unique capturing single-stranded sequences at both 3'- and 5'-end, restriction endonuclease recognition sites must be located with the adaptor sequences. In addition, to break the concatemers precisely at the junctions between the adaptors and the inserts, the restriction endonuclease cutting sites have to reside outside the associated recognition sites. This requirement reduces the pool of potential restriction enzymes to Type IIs restriction endonucleases. Other restriction enzyme requirements include (i) activity on double-stranded DNA only; (ii) the ability to cut close to the ends of double-stranded DNA; (iii) specific and unique cutting site and (iv) negligible star activity or wobble cutting. There are very few restriction endonucleases that meet all of these criteria. Four candidates were identified and characterized: BciV I, Dpn II, Hph I and TspR I. Dpn II and TspR I were confirmed to fulfill all of the above requirements (FIG. 8). It is worth noting that Type II restriction endonucleases have been shown to digest single stranded DNA (Nishigaki et al. (1985) *Nucl. Acids Res.* 13:5747. It was determined, however, that Dpn II, TspR I and Taqα I all specifically digested double stranded DNA using the conditions tested.

The entire circularization/amplification/digestion protocol was tested with a degenerate oligonucleotide synthesized by IDT, which mimicked a complex pool of chip-synthesized oligonucleotides (FIG. 8B). Approximately 30,000 padlock probes were successfully generated from Agilent's oligonucleotides using this probe releasing method.

EXAMPLE IV

MIP-Based Genotyping with Padlock Probes (Step 8-10)

Figure 9A:
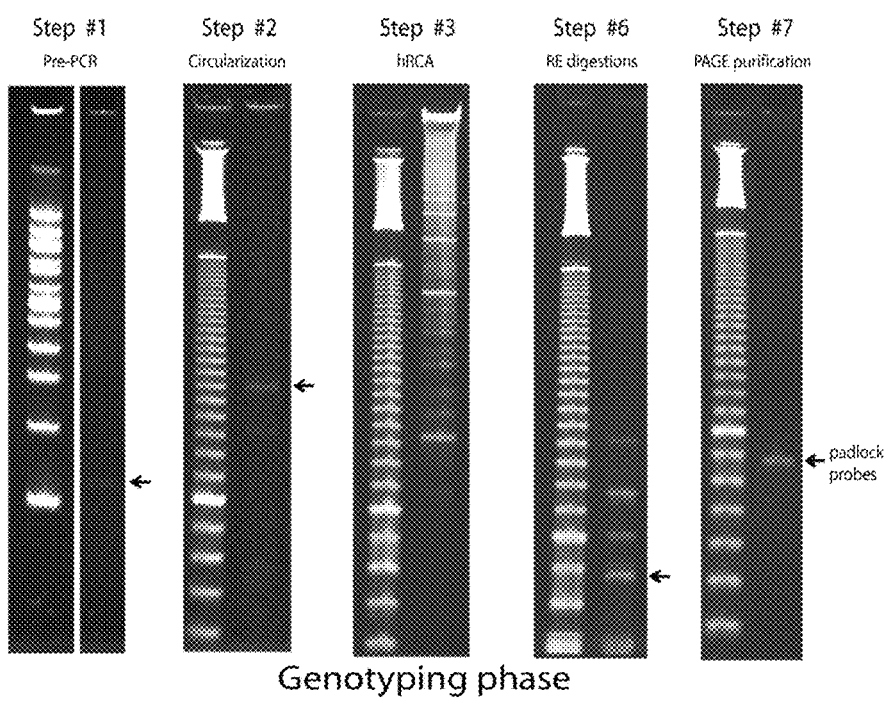
FIGS. 9A-9B depict a pilot synthesis and genotyping experiment with 29,908 Agilent oligos. (A) shows the synthesis phase. The products of several key steps were characterized by PAGE analyses. (B) shows the genotyping phase. A set of padlock probes generated in the synthesis phage was used to genotype a HAPMAP DNA sample GM10835. A/T/G/C corresponds to four fill-in reactions with four different nucleotides and NNC is a no-nucleotide control. The left panel is PAGE gel analysis of the amplicons and the right panel depicts the real-time PCR amplification curves.
Figure 9B:
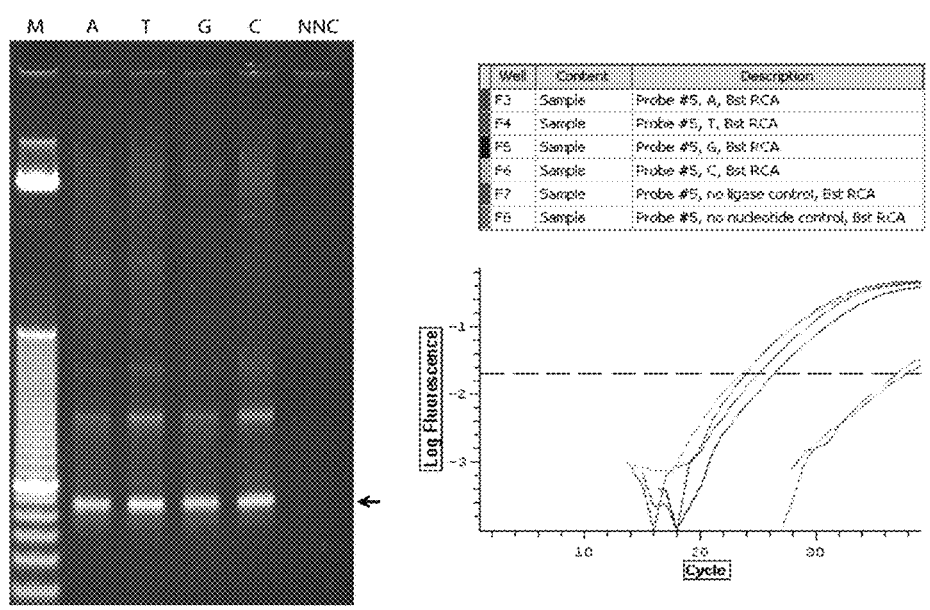

Using approximately 30,000 padlock probes generated from Agilent's oligonucleotides (FIG. 9A), three critical steps of technical development in the genotyping phase were tested (FIG. 9B). Although the protocol for allelic-specific extension and circularization (Step 8) had been well established (Hardenbol et al. (2003) *Nat. Biotechnol.* 21:673; Hardenbol et al. (2005) *Genome Res.* 15:269), two critical points were identified (using Apyrase to remove contaminating nucleotides; adding polymerase and ligase after probes are annealed to the genomic templates) to ensure specific extension and ligation.

It was also determined that, due to the low ligation efficiency on genomic templates, amplification of circularized padlock probes by PCR (Step 10) was associated with high amplification biases. However, it was also determined that a pre-PCR Rolling Circle Amplification using either Bst polymerase or phi29 polymerase reduced the biases dramatically. The genotyping assay was verified using Sanger Sequencing, and it was confirmed that the genotyping assay is specific. In addition, it was determined that, in designing padlock probes, SNPs located within repetitive regions of the human genome should not be included, because the corresponding padlock probes tended be present at very high copy numbers after circularization and reduce the efficiency of genotyping assay.

---

What is claimed is:

1. A method of analyzing a plurality of genomic DNA samples to obtain sequence information at one or more loci in each genomic DNA sample, the method comprising the steps of:
providing one or more probes having two regions of homology to target genomic DNA at the ends of the probe, two PCR primer regions common to all probes, and a bar code specific for a locus;
hybridizing the probes to immobilized genomic DNA such that the probe is hybridized in a circular manner to complementary genomic DNA;
ligating the probe to produce a closed circular molecule;
separating the closed circular molecule from the genomic DNA; and
ePCR amplifying the closed circular molecule, wherein the closed circular molecule is separated from the genomic DNA prior to amplifying, and wherein the closed circular molecule is not cleaved prior to the amplifying.

2. The method of claim 1, further comprising the step of digesting unligated products after the step of ligating and before the step of separating.

3. The method of claim 1, further comprising the step of cleaving the amplification product obtained by amplifying the closed circular molecule.

4. The method of claim 3, wherein cleaving is performed by a restriction enzyme.

5. The method of claim 1, wherein the one or more probes further comprise a universal detection tag sequence.

6. A method of analyzing a plurality of genomic DNA samples to obtain sequence information at one or more loci in each genomic DNA sample, the method comprising the steps of:
providing one or more probes having two regions of homology to target genomic DNA at the ends of the probe, two PCR primer regions common to all probes, and a bar code specific for a locus;
hybridizing the probes to immobilized genomic DNA such that the probe is hybridized in a circular manner to complementary genomic DNA;
ligating the probe to produce a closed circular molecule;
separating the closed circular molecule from the genomic DNA; and
polony amplifying the closed circular molecule, wherein the closed circular molecule is separated from the genomic DNA prior to amplifying, and wherein the closed circular molecule is not cleaved prior to the amplifying.

7. The method of claim 6, further comprising the step of polony sequencing.

8. A method of analyzing a plurality of genomic DNA samples to obtain sequence information at one or more loci in each genomic DNA sample, the method comprising the steps of:
providing one or more probes having two regions of homology to target genomic DNA at the ends of the probe, two PCR primer regions common to all probes, a bar code specific for a locus and a bar code specific for a patient;
contacting the probes with genomic DNA to hybridize the probe in a circular manner to complementary genomic DNA;
ligating the probe to produce a closed circular molecule;
separating the closed circular molecule from the genomic DNA; and
ePCR amplifying the closed circular molecule, wherein the closed circular molecule is separated from the genomic DNA prior to amplifying, and wherein the closed circular molecule is not cleaved prior to the amplifying.

9. The method of claim 8, further comprising the step of cleaving the amplification product obtained by amplifying the closed circular molecule using a restriction enzyme.

10. The method of claim 8, wherein the one or more probes further comprise a unique tag sequence.

11. A method of analyzing a plurality of genomic DNA samples to obtain sequence information at one or more loci in each genomic DNA sample, the method comprising the steps of:
providing one or more probes having two regions of homology to target genomic DNA at the ends of the probe, two PCR primer regions common to all probes, a bar code specific for a locus and a bar code specific for a patient;
contacting the probes with genomic DNA to hybridize the probe in a circular manner to complementary genomic DNA;
ligating the probe to produce a closed circular molecule;
separating the closed circular molecule from the genomic DNA; and
polony amplifying the closed circular molecule, wherein the closed circular molecule is separated from the genomic DNA prior to amplifying, and wherein the closed circular molecule is not cleaved prior to the amplifying.

12. The method of claim 11, further comprising the step of polony sequencing.

13. A method of analyzing a plurality of genomic DNA samples to obtain sequence information at one or more loci in each genomic DNA sample, the method comprising the steps of:
providing one or more probes having two regions of homology to target genomic DNA at the ends of the probe, two PCR primer regions common to all probes, and a bar code specific for a locus;
hybridizing the probes to immobilized genomic DNA such that the probe is hybridized in a circular manner to complementary genomic DNA with a one or more nucleotide gap between the ends of the circularized probe;
polymerizing the extension of the probe in the presence of dATP, dCTP, dGTP or dTTP and a polymerase;
ligating the probe to produce a closed circular molecule;
separating the closed circular molecule from the genomic DNA; and ePCR amplifying the closed circular molecule, wherein the closed circular molecule is separated from the genomic DNA prior to amplifying, and wherein the closed circular molecule is not cleaved prior to the amplifying.

14. The method of claim 13, further comprising the step of digesting unligated products after the step of ligating and before the step of separating.

15. The method of claim 13, further comprising the step of cleaving the amplification product obtained by amplifying the closed circular molecule.

16. The method of claim 15, wherein cleaving is performed by a restriction enzyme.

17. The method of claim 13, wherein the one or more probes further comprise a universal detection tag sequence.

18. A method of analyzing a plurality of genomic DNA samples to obtain sequence information at one or more loci in each genomic DNA sample, the method comprising the steps of:
providing one or more probes having two regions of homology to target genomic DNA at the ends of the probe, two PCR primer regions common to all probes, and a bar code specific for a locus;
hybridizing the probes to immobilized genomic DNA such that the probe is hybridized in a circular manner to complementary genomic DNA with a one or more nucleotide gap between the ends of the circularized probe;
polymerizing the extension of the probe in the presence of dATP, dCTP, dGTP or dTTP and a polymerase;
ligating the probe to produce a closed circular molecule;
separating the closed circular molecule from the genomic DNA; and
polony amplifying the closed circular molecule, wherein the closed circular molecule is separated from the genomic DNA.

19. The method of claim 18, further comprising the step of polony sequencing.

20. A method of analyzing a plurality of genomic DNA samples to obtain sequence information at one or more loci in each genomic DNA sample, the method comprising the steps of:
providing one or more probes having two regions of homology to target genomic DNA at the ends of the probe, two PCR primer regions common to all probes, a bar code specific for a locus and a bar code specific for a patient;
contacting the probes with genomic DNA to hybridize the probe in a circular manner to complementary genomic DNA with a one or more nucleotide gap between the ends of the circularized probe;
polymerizing the extension of the probe in the presence of dATP, dCTP, dGTP or dTTP and a polymerase;
covalently attaching the extension to the end of the probe in the presence of a ligase to produce a closed circular molecule; and
ePCR amplifying the closed circular molecule, wherein the closed circular molecule is separated from the genomic DNA prior to amplifying, and wherein the closed circular molecule is not cleaved prior to the amplifying.

21. The method of claim 20, further comprising the step of cleaving the amplification product obtained by amplifying the closed circular molecule using a restriction enzyme.

22. The method of claim 20, wherein the one or more probes further comprise a unique tag sequence.

23. A method of analyzing a plurality of genomic DNA samples to obtain sequence information at one or more loci in each genomic DNA sample, the method comprising the steps of:
providing one or more probes having two regions of homology to target genomic DNA at the ends of the probe, two PCR primer regions common to all probes, a bar code specific for a locus and a bar code specific for a patient;
contacting the probes with genomic DNA to hybridize the probe in a circular manner to complementary genomic DNA with a one or more nucleotide gap between the ends of the circularized probe;
polymerizing the extension of the probe in the presence of dATP, dCTP, dGTP or dTTP and a polymerase;
covalently attaching the extension to the end of the probe in the presence of a ligase to produce a closed circular molecule; and
polony amplifying the closed circular molecule, wherein the closed circular molecule is separated from the genomic DNA prior to amplifying, and wherein the closed circular molecule is not cleaved prior to the amplifying.

24. The method of claim 23, further comprising the step of polony sequencing.

* * * * *

UNITED STATES PATENT AND TRADEMARK OFFICE
CERTIFICATE OF CORRECTION

PATENT NO. : 10,036,055 B2  
APPLICATION NO. : 14/284764  
DATED : July 31, 2018  
INVENTOR(S) : Church et al.

Page 1 of 1

It is certified that error appears in the above-identified patent and that said Letters Patent is hereby corrected as shown below:

In the Specification

Column 1, under STATEMENT OF GOVERNMENT INTERESTS, Line 19-22:
Please delete "This application was funded in part by National Institutes of Health Grant No. HG003170 and Department of Energy Grant No. DE-FG02-02ER63445. The government has certain rights to the invention." and insert --This invention was made with government support under HG003170 awarded by National Institutes of Health (NIH) and under DE-FG02-02ER63445 awarded by U.S. Department of Energy (DOE). The government has certain rights in this invention.--

Signed and Sealed this
Twenty-seventh Day of September, 2022

Katherine Kelly Vidal
*Director of the United States Patent and Trademark Office*